(12) United States Patent
Sleiman et al.

(10) Patent No.: US 8,324,358 B2
(45) Date of Patent: Dec. 4, 2012

(54) POLYMER COMPOSITIONS AND USES THEREOF

(75) Inventors: Hanadi Sleiman, Montréal (CA); Bingzhi Chen, Harleysville, PA (US); Kim Metera, Montréal (CA)

(73) Assignee: McGill University, Montreal (CA)

( * ) Notice: Subject to any disclaimer, the term of this patent is extended or adjusted under 35 U.S.C. 154(b) by 475 days.

(21) Appl. No.: 11/914,721

(22) PCT Filed: May 26, 2006

(86) PCT No.: PCT/CA2006/000866
§ 371 (c)(1),
(2), (4) Date: Jul. 7, 2008

(87) PCT Pub. No.: WO2006/130955
PCT Pub. Date: Dec. 14, 2006

(65) Prior Publication Data
US 2009/0130665 A1 May 21, 2009

Related U.S. Application Data

(60) Provisional application No. 60/684,960, filed on May 27, 2005.

(51) Int. Cl.
*C07H 21/00* (2006.01)
*C07H 21/02* (2006.01)
*C12Q 1/68* (2006.01)

(52) U.S. Cl. ............ 536/23.1; 536/24.3; 536/26.6; 435/6.1

(58) Field of Classification Search ............ 536/23.1, 536/24.3, 26.6; 435/6.1
See application file for complete search history.

(56) References Cited

U.S. PATENT DOCUMENTS 5,990,479 A 11/1999 Weiss et al. ............ 850/56

OTHER PUBLICATIONS

Chen et a.l, "Biotin-terminated ruthenium bipyridine ring-opening metathesis polymerization copolymers: Synthesis and self-assembly with streptavidin," *Macromolecules*, 38(4):1084-1090, 2005.

Chen et al., "Novel fluorene-alt-thienylenevinylene-based copolymers: tuning luminescent wavelength via thiopene substitution position," *Eur. Polymer. Journal.*, 40(6):1183-1191, 2004.

Chen et al., "Ruthenium bipyridine-containing polymers and block copolymers via ring-opening metathesis polymerization," *Macromolecules*, 37:5866-5872, 2004.

Dequaire et al., "Biotinylation of screen-printed carbon electrodes through the electrochemical reduction of the diazonium salt of p-aminobenzoyl biocytin," *J. Am. Chem. Soc.*, 121:6946-6947, 1999.

Gohy et al., "From supramolecular block copolymers to advanced nano-objects," *Chem. Eur. J.*, 9:3472-3479, 2003.

(Continued)

*Primary Examiner* — Jezia Riley
(74) *Attorney, Agent, or Firm* — Fulbright & Jaworski L.L.P.

(57) ABSTRACT

Block copolymers labelled with molecular recognition units and comprising a hydrophobic block and a luminescent block are presented. A method of detecting biomolecules using such block copolymers is also presented. More specifically, the block copolymers of the present invention have the following Formula (I): wherein "A" is a hydrophobic block; "B" is a luminescent block; "C" is a hydrophilic block; "D" is a molecular recognition unit; "n" and "m" are integers ranging from 1 to 75; "x" is either 0 or an integer ranging from 1 to 75; and "Y" is either 0 or 1.

18 Claims, 5 Drawing Sheets

OTHER PUBLICATIONS

Gohy et al., "Reversible metallo-supramolecular block copolymer micelles containing a soft core," *Macrol. Rapid Commun.*, 23(9):555-560, 2002.

Gruber et al., "Biotin-fluorophore conjugates with poly(ethylene glycol) spacers retain intense fluorescence after binding to avidin and streptavidin," *Bioconjugate Chem.*, 8(4):552-559, 1997.

Heldt et al., "Preparation and characterization of poly(amidoamine) dendrimers functionalized with a rhenium carbonyl complex and a PEG as a new IR probes for carbonyl metallo immunoassay," *J. Organometallic Chemistry*, 689(25):4775-4782, 2004.

Hofmeier et al., "Combined biotin-terpyridine systems: A new versatile bridge between biology, polymer science and metaollo-supramolecular chemistry," *Biomacromolecules*, 5(5):2055-2064, 2004.

Lee et al., "Synthesis of novel electochemiluminescent polyamine dendrimers functionalized with polypyridyl Ru(II) complexes and their electrochemical properties," *Bull. Korean Chem. Soc.*, 27(1):99-105, 2006.

Lo et al., "Luminescent ruthenium (II) polypyridine biotin complexes: Synthesis, characterization, photophysical and electrochemical properties, and avidin-binding studies," *Inorg. Chem.*, 43(17):5275-5282, 2004.

Lo et al., "Luminescent transition metal polypyridine biotin complexes," *Journal of the Chinese Chemical Society*, 53(1):53-65, 2006.

Lohmeijer et al., "Playing LEGO with macromolecules; Design, synthesis and self-organisation with metal complexes," *J. Polymer Science: Part A: Polymer Chemistry*, 41:1413-1427, 2003.

Luo et al., "Mono-bisthienylethene ring-fused versus multi-bisthienylethene ring-rused photochromic hybrids," *Adv. Fund. Mater.*, 13(3):233-239, 2003.

Marek et al., "Biotin-pyrene conjugates with poly(ethylene glycol) spaces are convenient fluourescent probes for abiding and streptavidin," *Bioconjusgate Chem.*, 8:560-566, 1997.

PCT International Search Report and Written Opinion issued in International application No. PCT/CA2006/00086, dated Sep. 12, 2006.

Rezvani et al., "Ruthenium (II) dipyridoquinoxaline-norbornene: Synthesis, properties, crystal structure and use as a ROMP monomer," *Inorg. Chem.*, 43:5112-5119, 2004.

Slim et al., "Ruthenium (II)-phenanthroline-biotin complexes: Synthesis and luminescence enhancement upon binding to avidin," *Bioconjugate Chemistry*, 15(5):949-953, 2004.

Wang et al., "Photochromic copolymers containing bisthienylethene units," *Macromol. Chem. Phys.*, 205:1467-1507, 2004.

POLYMER COMPOSITIONS AND USES THEREOF

CROSS-REFERENCE TO RELATED APPLICATIONS

The present application is a national phase application under 35 U.S.C. §371 of International Application No. PCT/CA2006/000866 filed 26 May 2006, which claims the benefit of U.S. Provisional Application No. 60/684,960 filed 27 May 2005. The entire contents of these applications are incorporated by reference.

FIELD ON THE INVENTION

The present invention relates to polymer compositions. More specifically, but not exclusively, the present invention relates to novel luminescent polymer bio-conjugates and uses thereof.

BACKGROUND OF THE INVENTION

One of the major current scientific challenges is to identify the function and expression of human genes. A better appreciation of such function and expression contributes to an enhanced understanding of human health, provides for a more accurate diagnosis of human diseases as well as providing for a more targeted design of medical therapies. Accordingly, the area of gene detection has witnessed a tremendous amount of research activity in recent years.

DNA and RNA samples are usually isolated from cellular material in very small quantities, calling upon techniques for signal enhancement. However, while many DNA detection methods have been designed, the various difficulties associated with signal enhancement remain unresolved.

To date, techniques for signal enhancement of gene detection have typically relied upon the enzymatic amplification of the analyte. The polymerase chain reaction (PCR) has become a standard technique in almost every molecular biology laboratory for the amplification of targeted DNA or RNA sequences. However, PCR techniques can be time consuming and may not preserve all the information contained within the DNA or RNA sequences to be analyzed.

Detecting minute concentrations of physiological or aberrant proteins is essential for correlation with pathologic state, diagnosing disease or monitoring disease progression. For proteins, however, in vitro methods allowing for signal amplification of the detection event are not readily available.

Organic chromophores, which are commonly used in biological assays, often undergo self-quenching, severely limiting their use as signal amplification systems. Ruthenium tris-bipyridine, a luminescent and redox active transition metal complex, does not exhibit significant self-quenching because of its large Stokes shift (i.e., its absorption and emission spectra do not overlap).

Several systems have been reported to affect signal amplification of biomolecules. In one method, dendrimers containing as many as eight ruthenium centers have been described, and in two systems, the dendrimers have been covalently attached to a protein, or to progesterone.[1] Amplification in both the luminescence and the electrochemiluminescence signals was detected.

Another system reported by Bard et al. describes the encapsulation of free ruthenium tris-bipyridine complexes in polystyrene microspheres. The microspheres are labeled with single stranded DNA (analyte). These microspheres were then used to capture magnetic particles labeled with probe complementary DNA. Redissolution of these microspheres liberated the ruthenium centers, which were detected with electrochemiluminescence.[2] However, physically entrapping the ruthenium centers within the reported microspheres raises the possibility of premature leaking, which in turn can interfere with the specificity of the biological recognition event.

In yet another method, polyacrylonitrile nanospheres were doped with ruthenium bipyridine units, and their luminescence studied. However, these doped nanospheres have not been used for biological assays.[3]

Silica nanoparticles doped with ruthenium bipyridine units have been reported, and have been used for DNA and protein assays.[4] However, such silica based nanoparticle systems have significant limitations. While a certain number of chromophores may be physically entrapped within the silica particles, there is little control over: (i) how many ruthenium centers may be encapsulated; (ii) the location of the ruthenium centers within the particle; and (iii) if more than one type of chromophore is used, there is limited control over the ratio. Moreover, the particles cannot be subsequently opened and the ruthenium bipyridine centers cannot be liberated for electrochemiluminescence, thus limiting signal amplification to mere luminescence.

An ultrasensitive assay, using both gold and magnetic particles labeled with DNA, as well as a multistep method involving silver enhancement has also been reported.[5]

Ruthenium bipyridine-containing polymers have recently been the subject of increasing interest, due to their numerous potential applications (i.e. photoconductive materials, photocatalysts, solar energy conversion materials, sensors, and supramolecular building blocks).[6-14] Ruthenium bipyridine complexes present additional unique photophysical properties which distinguish them from their organic counterparts, including their long excited-state lifetimes, chemical inertness and photostability, tunability of their photophysical characteristics, large Stokes shifts and resistance to photobleaching.[15-17] The incorporation of many of these chromophores into a polymeric backbone provides one way of amplifying a luminescence signal triggered by the recognition of a biological molecule.[18]

To achieve an even greater degree of luminescence amplification, block copolymers comprising repeating ruthenium (II) bipyridine chromophore units have been constructed.[19] Self-assembly of these copolymers yields luminescent nanoscale micellar aggregates, containing a large number of ruthenium (II) chromophores.

There thus remains a need for methods allowing for the rapid and highly sensitive detection of specific biomolecules in a sample through signal amplification. Moreover, there remains a need for compositions and articles of manufacture useful in such a method.

The present invention seeks to meet these needs and other needs.

The present description refers to a number of documents, the content of which is herein incorporated by reference in their entirety.

FIELD OF THE INVENTION

The present invention relates to polymer compositions allowing for the rapid and highly sensitive detection of biomolecules in a sample through signal amplification. In an embodiment, the present invention relates to block copolymers labeled with molecular recognition units and comprising a hydrophobic block and a luminescent block. In an embodiment, the present invention relates to luminescent polymer bio-conjugates that assemble into nanoparticles thereby enabling cellular imaging and the detection of analyte molecules (i.e. biomolecules) through signal amplification.

The present invention relates to a block copolymer of Formula:

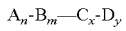
$A_n\text{-}B_m\text{—}C_x\text{-}D_y$ wherein "A" is a hydrophobic block; "B" is a luminescent block; "C" is a hydrophilic block; "D" is a molecular recognition unit; "n" and "m" are integers ranging from 1 to 75; "x" is either 0 or an integer ranging from 1 to 75; and "Y" is either 0 or 1.

The present invention relates to polymer compositions as well as assays comprising such compositions, that associate the analyte biomolecule to be detected (i.e. nucleic acid, protein) with a large number of luminescent centers.

The present invention relates to polymer compositions allowing for the rapid and highly sensitive detection of oligonucleotides and polynucleotides.

The present invention relates to polymer compositions allowing for the rapid and highly sensitive detection of exceedingly small quantities of protein expression.

The present invention relates to polymer compositions allowing for the rapid and highly sensitive detection of enzymes.

The present invention relates to a nucleic acid detection system comprising at least one block copolymer as defined herein, the block copolymer being biotinylated; an oligonucleotide probe mounted on a solid support and a biotinylated reporter oligonucleotide sequence; a protein selected from the group consisting of avidin and streptavidin; wherein the probe and the reporter sequence comprise respective sequences, each respective sequence being complementary to a nucleic acid analyte, thereby providing for the probe and the reporter to respectively detect the nucleic acid analyte, thereby obtaining a biotinylated solid-supported analyte, the supported analyte being allowed to be labeled with the copolymer by means of the protein to provide analyte labeled particles that are detectable by observing luminescent emissions upon excitation.

Moreover, the present invention relates to a method of detecting the presence of a target polynucleotide comprising: providing a biotinylated block copolymer as defined herein; contacting a target polynucleotide analyte with a solid-supported oligonucleotide probe and a biotinylated reporter oligonucleotide sequence, wherein the probe and the reporter sequence comprise respective sequences, each of the respective sequences being complementary to the target polynucleotide, thereby obtaining a biotinylated solid-supported analyte; contacting the supported analyte with the biotinylated block copolymer using avidin or streptavidin; and detecting luminescent emissions indicative of the presence of the target polynucleotide.

Finally, the present invention relates to a use of a block copolymer labeled with molecular recognition units and comprising a hydrophobic block and a luminescent block, for detecting an analyte biomolecule. In an embodiment of the present invention, the block copolymer is used for detecting oligonucleotides and polynucleotides. In a further embodiment of the present invention, the block copolymer is used for detecting proteins. In yet a further embodiment of the present invention, the block copolymer is used for detecting enzymes.

The foregoing and other objects, advantages and features of the present invention will become more apparent upon reading of the following non restrictive description of illustrative embodiments thereof, given by way of example only with reference to the accompanying drawings.

DETAILED DESCRIPTION OF ILLUSTRATIVE EMBODIMENTS

Figure 1:
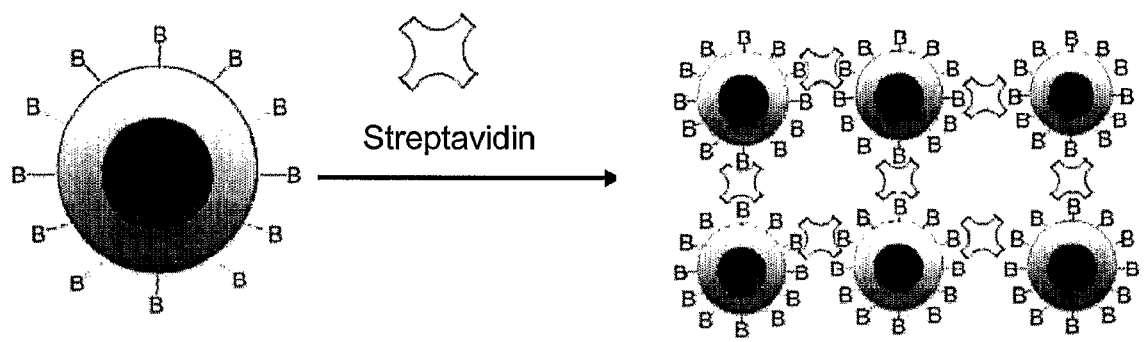
FIG. 1 is an illustration of the aggregation of biotinylated nanospheres by streptavidin in accordance with an embodiment of the present invention.
Figure 2:
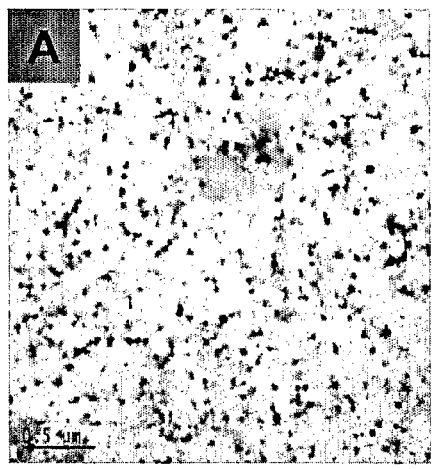
FIG. 2 is an illustration of Transmission Electron Microscopy (TEM) images (left column images A, C) of an aqueous micelle solution of copolymer 2 prior to addition of streptavidin at different magnifications; of Transmission Electron Microscopy images (right column images B, D) of an aqueous micellar solution of copolymer 2 following addition of streptavidin; of a Transmission Electron Microscopy image (E) of an aqueous micelle solution of copolymer 22 prior to addition of streptavidin; and of a Transmission Electron Microscopy image (F) of an aqueous micelle solution of copolymer 22 following addition of streptavidin (3 h).
Figure 2:
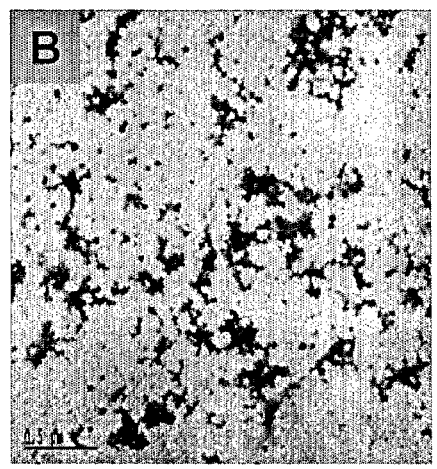
Figure 2:
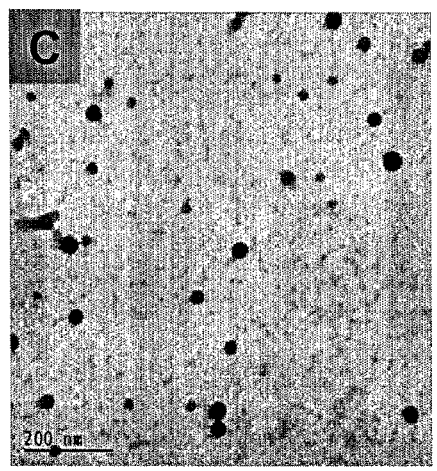
Figure 2:
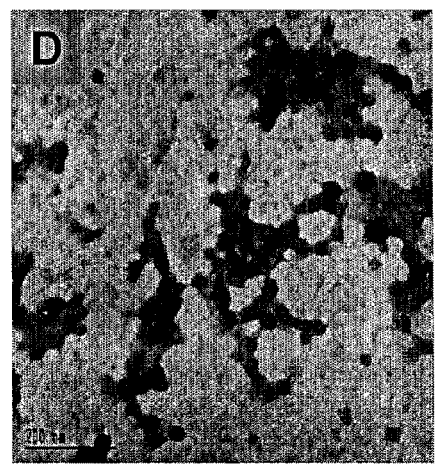
Figure 2:
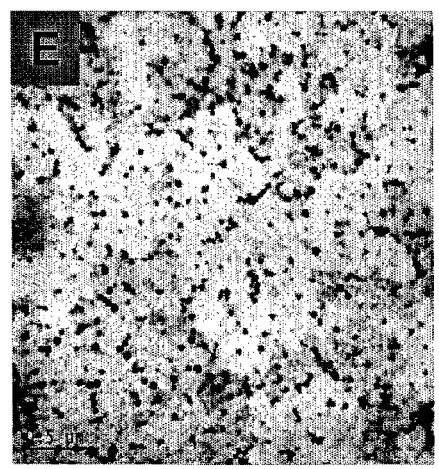
Figure 2:
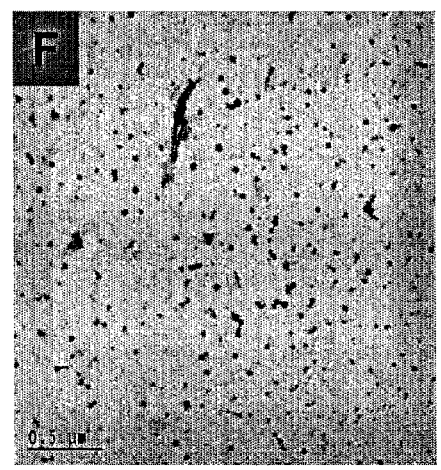
Figure 3:
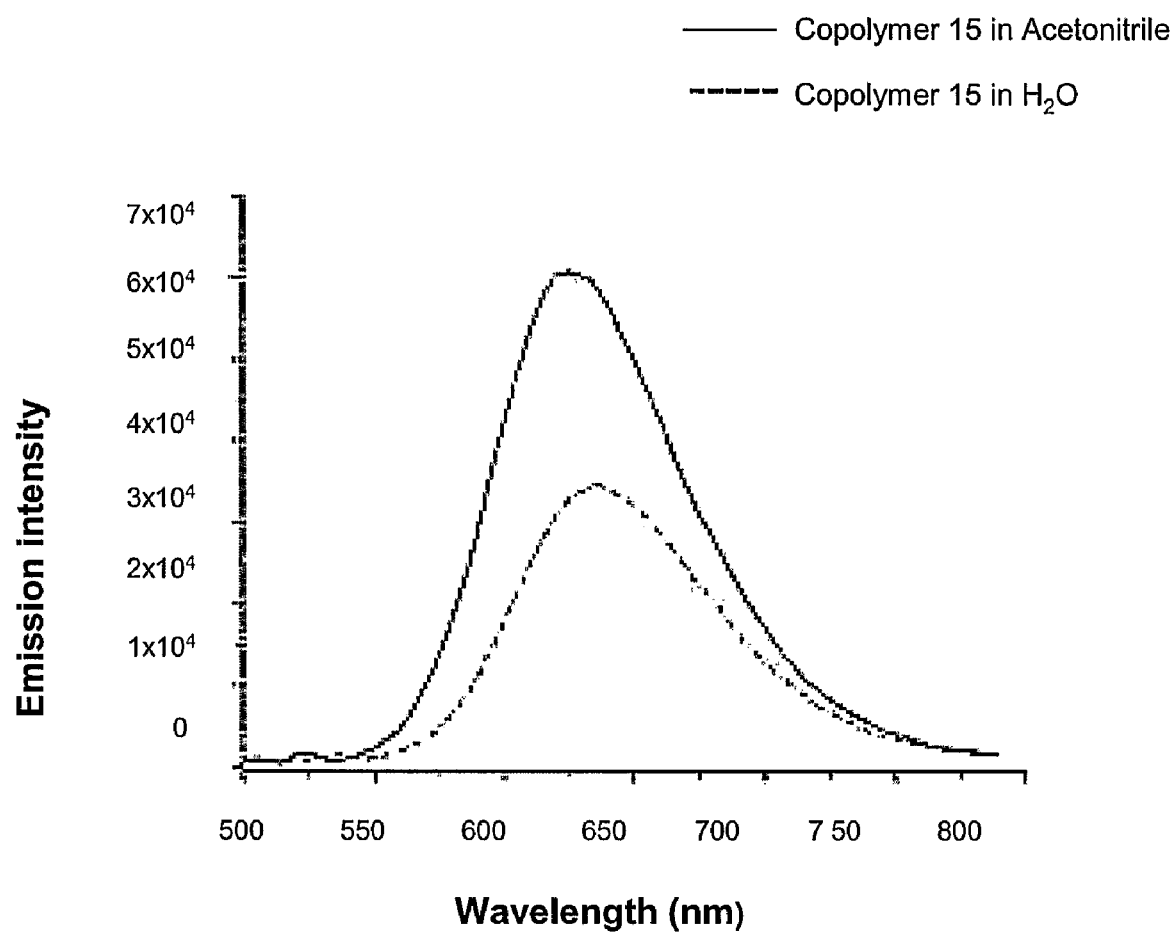
FIG. 3 is an illustration of the emission spectra of copolymer 15 in acetonitrile (where the copolymer chains are free) and in water (where the copolymer self-assembles into micellar aggregates)

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The present description refers to a number of chemical terms and abbreviations used by those skilled in the art. Nevertheless, definitions of selected terms are provided for clarity and consistency.

Abbreviations: TEM: Transmission Electron Microscopy; ROMP: Ring-Opening Metathesis Polymerization; ECL: ElectroChemiLuminescence; DMF: Dimethylformamide;

DEAD: Diethyl azodicarboxylate; THF: Tetrahydrofuran; DMAP: N,N-Dimethylpyridine.

The term "alkyl", as used herein, is understood as referring to saturated straight-chain or branched hydrocarbon radicals having from 1 to 18 carbon atoms. Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

The term "aromatic", as used herein, is understood as referring to aromatic monocyclic or fused polycyclic ring structure having a total of from 6 to 18, preferably 6 to 10, ring carbon atoms (no heteroatoms). Exemplary aryl groups include phenyl, naphthyl, anthracenyl, and the like.

The term "biomolecule", as used herein, is understood as referring to molecules (e.g., proteins, amino acids, nucleic acids, nucleotides, carbohydrates, sugars, lipids, etc.) that are found in nature. The terms "biomolecule" and "analyte" are used interchangeably.

The term "luminescence", as used herein, is understood as referring to the process of emitting electromagnetic radiation (e.g., light). Luminescence results when a system undergoes a transition from an excited state to a lower energy state, with a corresponding release of energy in the form of a photon. These energy states can be electronic, vibrational, rotational, or any combination thereof. The transition responsible for luminescence can be stimulated through the release of energy stored in the system chemically, kinetically, or added to the system from an external source. The external source of energy can be of a variety of types including chemical, thermal, electrical, magnetic, electromagnetic, or physical, or any other type of energy source capable of causing a system to be excited into a state higher in energy than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy X-ray radiation. Typically, luminescence refers to electromagnetic radiation in the range from UV to IR radiation, and usually refers to visible electromagnetic radiation (i.e., light).

The term "nanoparticle", as used herein, is understood as referring to a particle having a diameter in the range of about 1 nm to about 1000 nm, preferably in the range of about 2 nm to about 100 nm, more preferably in the range of about 20 nm to about 60 nm.

The present invention relates to block copolymers labeled with molecular recognition units and comprising a hydrophobic block and a luminescent block. The present invention further relates to a method allowing for the rapid and highly sensitive detection of specific biomolecules in a sample through signal amplification, the method comprising providing a block copolymer labeled with molecular recognition units and comprising a hydrophobic block and a luminescent block. Moreover, the present invention relates to compositions and articles of manufacture useful in such a method.

Contrary to many of the prior art methods and probes, the block copolymers of the present invention do not rely on any amplification techniques for detecting a given analyte (i.e. biomolecule) in a sample. Instead, the block copolymers of the present invention provide for the amplification of the signal that may be emitted by the analyte itself rather than amplifying the concentration of the specific analyte being detected.

The amplification of the signal that may be emitted by an analyte is achieved by means of a block copolymer labeled with molecular recognition units and comprising a hydrophobic block and a luminescent block. In an embodiment of the present invention, the block copolymer is labeled with the biological ligand biotin.

The nature of the polymerization reaction used to produce the block copolymers of the present invention should be such that well-defined polymers having a narrow molecular weight distribution are obtained. Moreover, the polymerization reaction should be functional group tolerant. The ring-opening metathesis polymerization reaction (ROMP) fulfils both requirements.[20]

The block copolymers of the present invention comprise a large number of luminescent molecules (i.e. chromophores). The synthesis of the block copolymers of the present invention was designed to accommodate the attachment of large numbers of chromophores to the polymer backbone without quenching of their luminescence as a result of their proximity. Self-assembly of these copolymers yields luminescent nanoscale micellar aggregates, containing large numbers of chromophores. When labeled with molecular recognition units, these micelles act as strong luminescent markers for specific biological molecules. In an embodiment of the present invention the chromophore is a ruthenium (II) bipyridine chromophore.

To access block copolymers suitable for biomolecule detection, a method to end-functionalize the polymers with a molecular recognition unit was devised. While the end-termination of ROMP polymers generated using the Schrock molybdenum-based catalyst is relatively straightforward, fewer reports have described this process for the more functional group tolerant ruthenium-based catalysts.[21] The creation of telechelic ROMP polymers with functional groups at both ends, by carrying out the ROMP reaction in the presence of disubstituted olefins has been reported.[22] Kiessling et al. have generated end-functionalized neoglycopolymers by quenching the active ROMP polymer chain with functionalized enol ethers.[23]

The synthesis of ruthenium containing polymers and their self-assembly into micellar nanospheres is more convenient than the synthesis of dendrimers. A dendrimer comprising about 50 ruthenium centers is difficult to prepare at best, compared to a polymer backbone comprising the same number of ruthenium centers. Furthermore, while the polymers of the present invention can self-assemble into micellar nanospheres comprising in excess of 10 000 ruthenium centers, dendrimers do not assemble into higher-order units. The nanospheres, readily obtained via the self-assembly of the polymers of the present invention, provide a far superior level of signal amplification. Moreover, self-assembly into nanospheres provides for the added advantage that the ruthenium units become incorporated in the nanospheres and are thus chemically shielded from the biological medium, reducing the likelihood of non-specific binding. Furthermore, contrary to the use of microspheres which, due to their relatively large size, precludes the 1:1 linking of a microsphere to an analyte molecule, the nanospheres as obtained through the self-assembly of the polymers of the present invention are as small as 40-50 nm which provides for each analyte molecule to bind to one nanosphere. Since each of such nanospheres is associated with a large number of ruthenium centers a far superior level of signal amplification is obtained.

Covalently linking the chromophores to the polymer backbone prevents the chromophores from prematurely detaching from the polymer which may interfere with the specificity of the biological recognition event.

The present invention relates to block copolymers labeled with molecular recognition units and comprising a hydrophobic block and a luminescent block. In an embodiment, the present invention relates to block copolymers labeled with molecular recognition units and comprising a hydrophobic block and a luminescent block allowing for the rapid and highly sensitive detection of a DNA sequence analyte, an RNA sequence analyte, protein(s) and or other analytes. The block copolymers of the present invention associate the analyte or analytes to be detected with a large number of luminescent metal centers. The present invention also relates to a method allowing for the rapid and highly sensitive detection of specific biomolecules in a sample through signal amplification. Furthermore, the present invention relates to compositions and articles of manufacture useful in such a method.

The block copolymers of the present invention self-assemble into micellar nanospheres. Such nanospheres comprise from about 100 to about 400 polymer chains. In an embodiment of the present invention, the nanospheres comprise an average of about 200 polymer chains, wherein each polymer chain comprises from about 10 to about 100 ruthenium bipyridine centers covalently linked to each polymer chain. In a further embodiment of the present invention, the nanospheres comprise an average of about 200 polymer chains, wherein each polymer chain comprises about 50 ruthenium bipyridine centers covalently linked to each polymer chain. Thus, when an analyte molecule becomes associated with one of the polymeric nanospheres, it effectively becomes associated with about 10,000 luminescent ruthenium centers. It is within the capacity of a skilled technician that the number of luminescent centers can be readily increased by inserting longer ruthenium containing blocks. This results in an ever greater degree of signal amplification associated with the biological detection event.

The synthesis of representative examples of polymers and block copolymers as contemplated by the present invention is illustrated hereinbelow in Scheme 1. More specifically, in accordance with an embodiment of the present invention, block copolymers that are end-functionalized with biotin are illustrated.

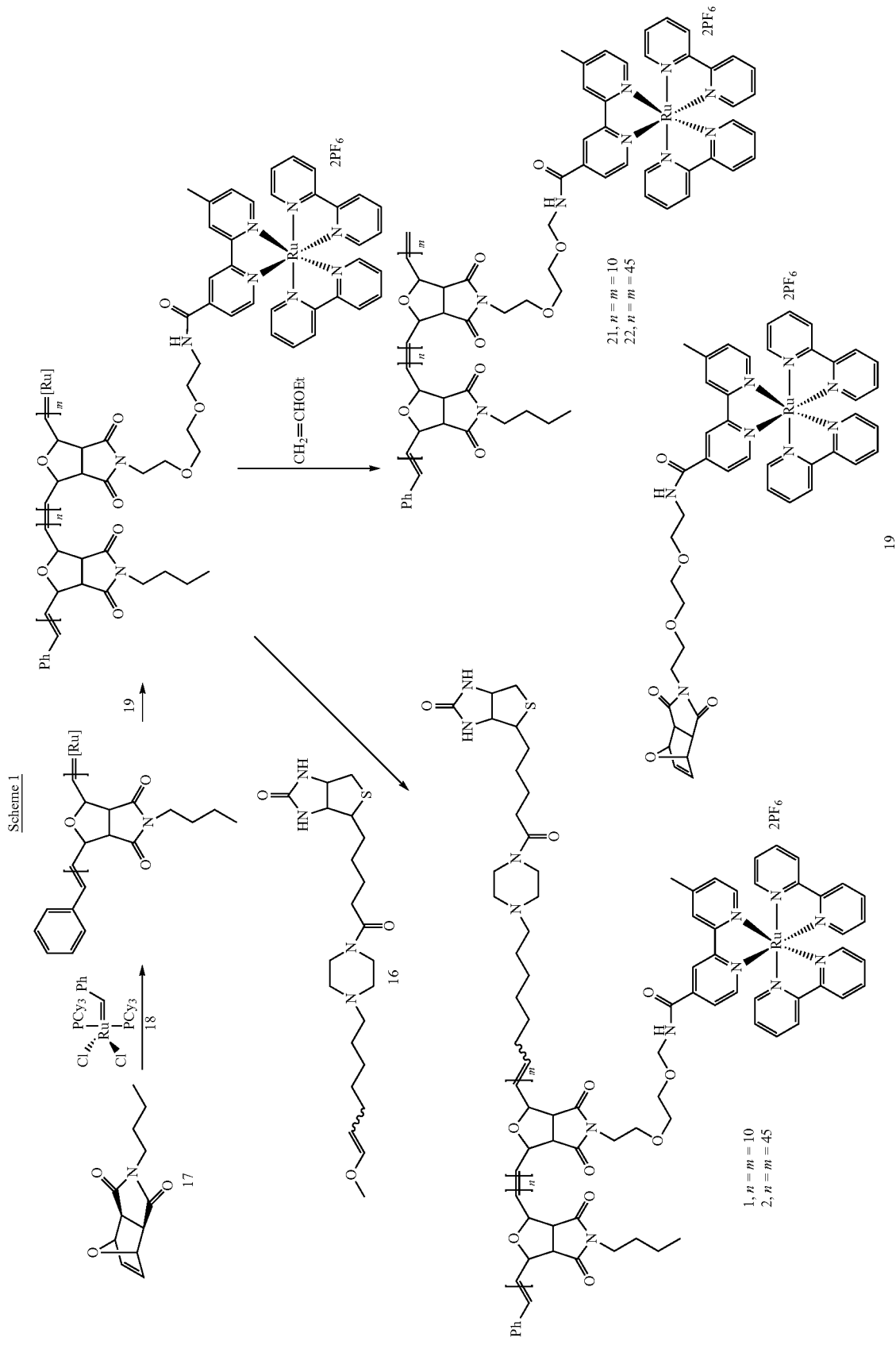

As illustrated hereinbelow in Scheme 2, polymers 13 and 15 comprise a hydrophobic block "A" that induces formation of micellar nanoparticles in water. Polymers 13 and 15 further comprise a luminescent block "B" comprising ruthenium centers as well as a molecular recognition unit "D" (i.e. biotin) covalently linked to one end of the polymer through a selected spacer.

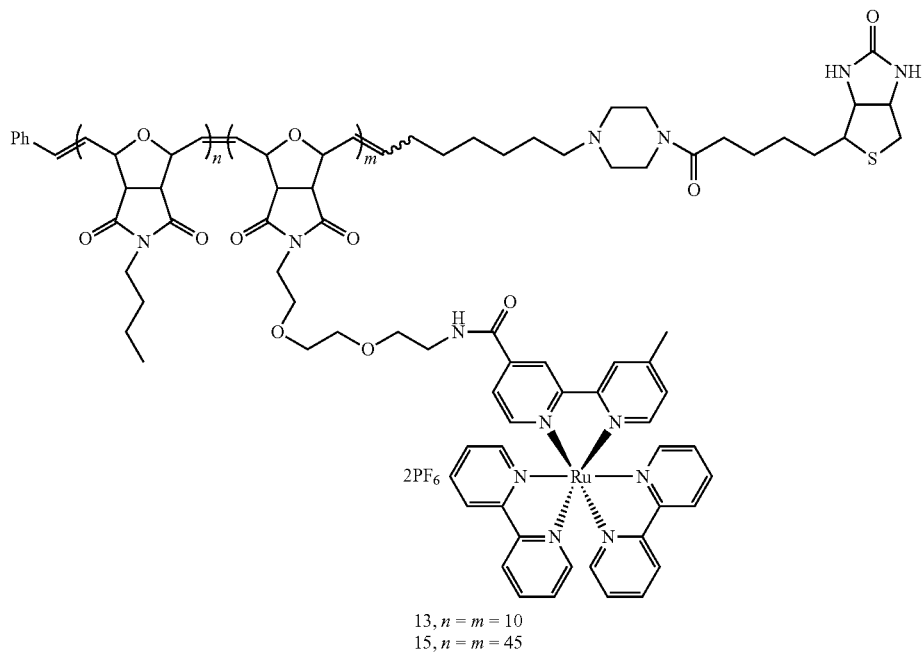

Scheme 2

13, $n = m = 10$
15, $n = m = 45$

Biotin has found widespread applications in bioassays. It is known to bind to the proteins avidin or streptavidin with high affinity ($K_d \sim 10^{-15}$ M). In addition, avidin or streptavidin can bind up to four biotin units, thus allowing it to act as a linker between two (or more) biotinylated molecules. Thus, the biotin units incorporated into the polymer systems of the present invention (i.e. 13 and 15) can act as a "molecular glue" to associate analyte biomolecules with a large number of luminescent units covalently linked to the backbone of 13 and 15. This is expected to greatly enhance the luminescence signal obtained upon a biological recognition event and as such permits the detection of exceedingly small amounts of a biomolecule (i.e. a specific DNA/RNA sequence, proteins, enzymes). In the case wherein specific DNA/RNA sequences are to be detected, the need for enzymatic amplification is eliminated by the greatly enhanced signal amplification.

A further representative example of a block copolymer as contemplated by the present invention is illustrated hereinbelow in Scheme 3. More specifically, in accordance with an embodiment of the present invention, block copolymer 5 wherein the biotin unit and the luminescent ruthenium units are separated by a hydrophilic unreactive polyethylene glycol block "C" is illustrated.

Scheme 3

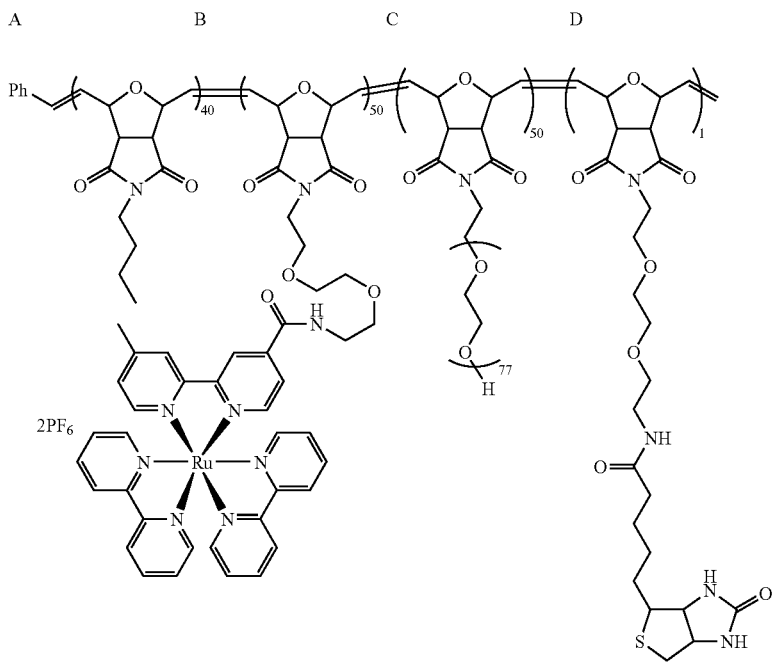

5

A further representative example of block copolymers as contemplated by the present invention is illustrated hereinbelow in Scheme 4. More specifically, in accordance with an embodiment of the present invention, a block of type "E" is illustrated which can be substituted for the luminescent ruthenium block in polymers 5, 13 and 15. It is within the capacity of a skilled technician that a block of type "E" can also be substituted for the luminescent ruthenium block "B" in other block copolymers as contemplated by the present invention.

Scheme 4

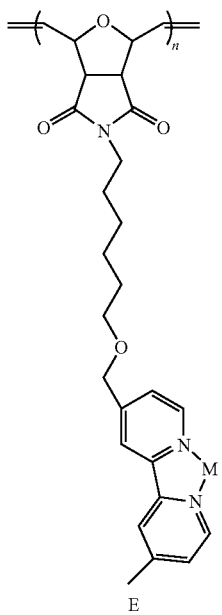

E

Block copolymers 5, 13 and 15 of the present invention associate the analyte or analytes to be detected with a large number of luminescent metal centers. Such association provides for signal amplification of a biological detection event as well as image biological targets through luminescence of the ruthenium bipyridine units. The wavelength of this luminescence is approximately 600 nm (orange).

As illustrated hereinbelow in Scheme 5, the bipyridine units may also be bound to numerous other metal complexes which emit at different wavelengths compared to the ruthenium bipyridine units. In an embodiment of the present invention, pyrene was appended to the monomers and polymers. The pyrene chromophores undergo aggregation to form excimers that emit at 475 nm (in the blue). Thus the polymers and compositions of the present invention offer the additional advantage of providing for nanoparticles including luminescent centers composed of one of these chromophores, as well as a combination of chromophores in a chosen predetermined ratio. Therefore, a very large set of nanoparticles of different colors can be created, and can be used for multiplexed biological assays, for example assays where several analytes are to be simultaneously detected. Alternatively, it is within the capacity of a skilled technician that a mixture of polymers, each comprising a given chromophore, can also be used.

Scheme 5

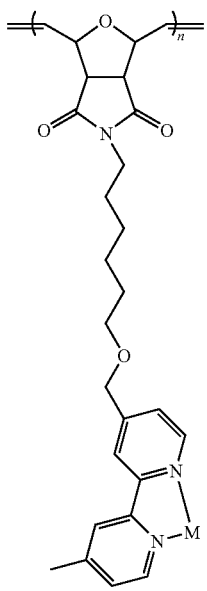

| M | Emission Wavelength |
| --- | --- |
| $Ru(bpy)_2^{2+}$ | 610 nm (orange) |
| $Os(bpy)_2^{2+}$ | 710 nm (red) |
| $Pt(C\equiv C-Ph)_2$ | 570 nm (yellow) |
| $Ru(diphenyl\ phosphinoethane)_2(CN)_2$ | 530 nm (green) |
| pyrene excimer | 475 nm (blue) |

EXPERIMENTAL

General. All reagents were obtained commercially and were used without further purification unless otherwise noted. Solvents were of reagent grade and if necessary, were dried by standard procedures. Monomers 5 and 11 were synthesized according to published procedures (Bazzi, H. S.; Bouffard, J.; Sleiman, H. F. *Macromolecules* 2003, 36, 7899; Chen, B. Z.; Sleiman, H. F. *Macromolecules* 2004, 37, 5866). $^1$H NMR and $^{13}$C NMR spectra were recorded on a Varian M300 spectrometer. The chemical shifts were reported in parts per million on the δ scale referenced to the deuterated solvent resonance. Fluorescence experiments were carried out on a Photon Technology International TimeMaster model C-720F spectrofluorimeter.

Assay for Detection of DNA

Figure 4:
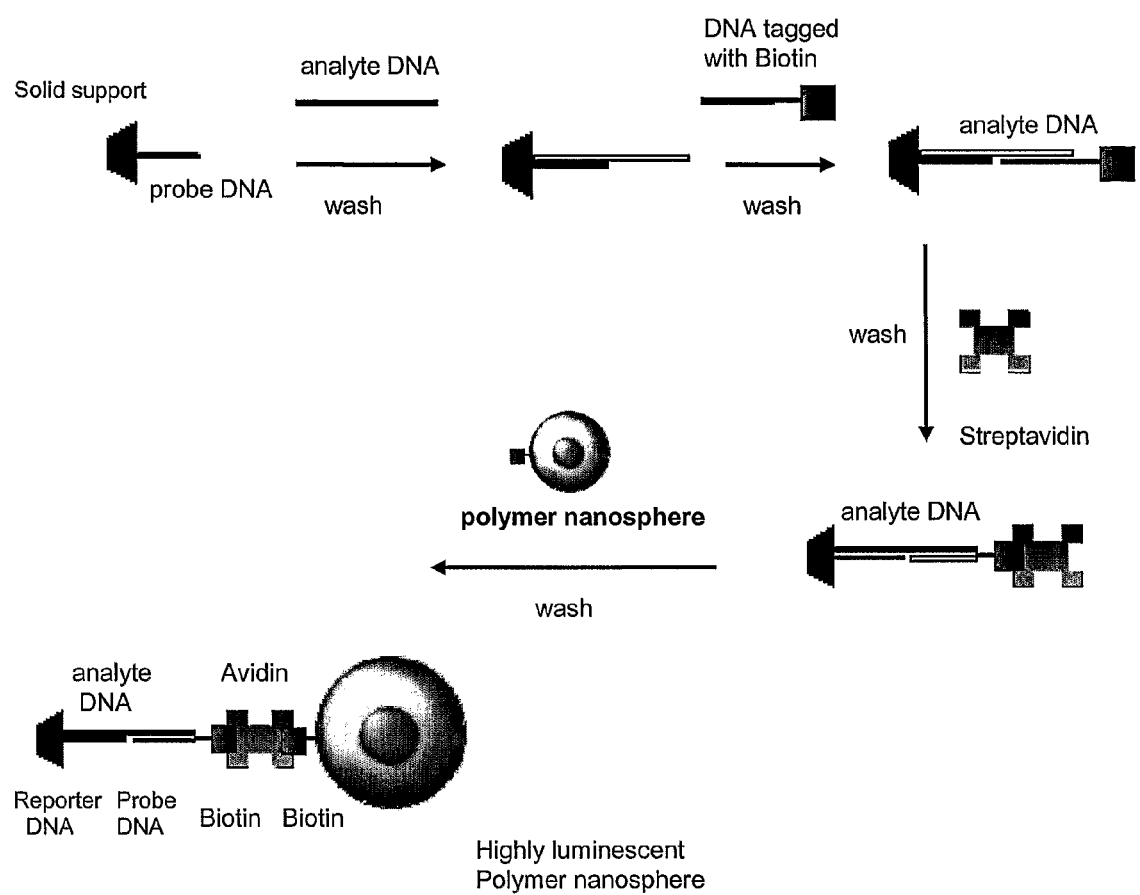
FIG. 4 is a schematic illustration of the use of a block copolymer in an assay in accordance with an embodiment of the present invention, providing for the detection of a targeted DNA sequence.
Figure 5:
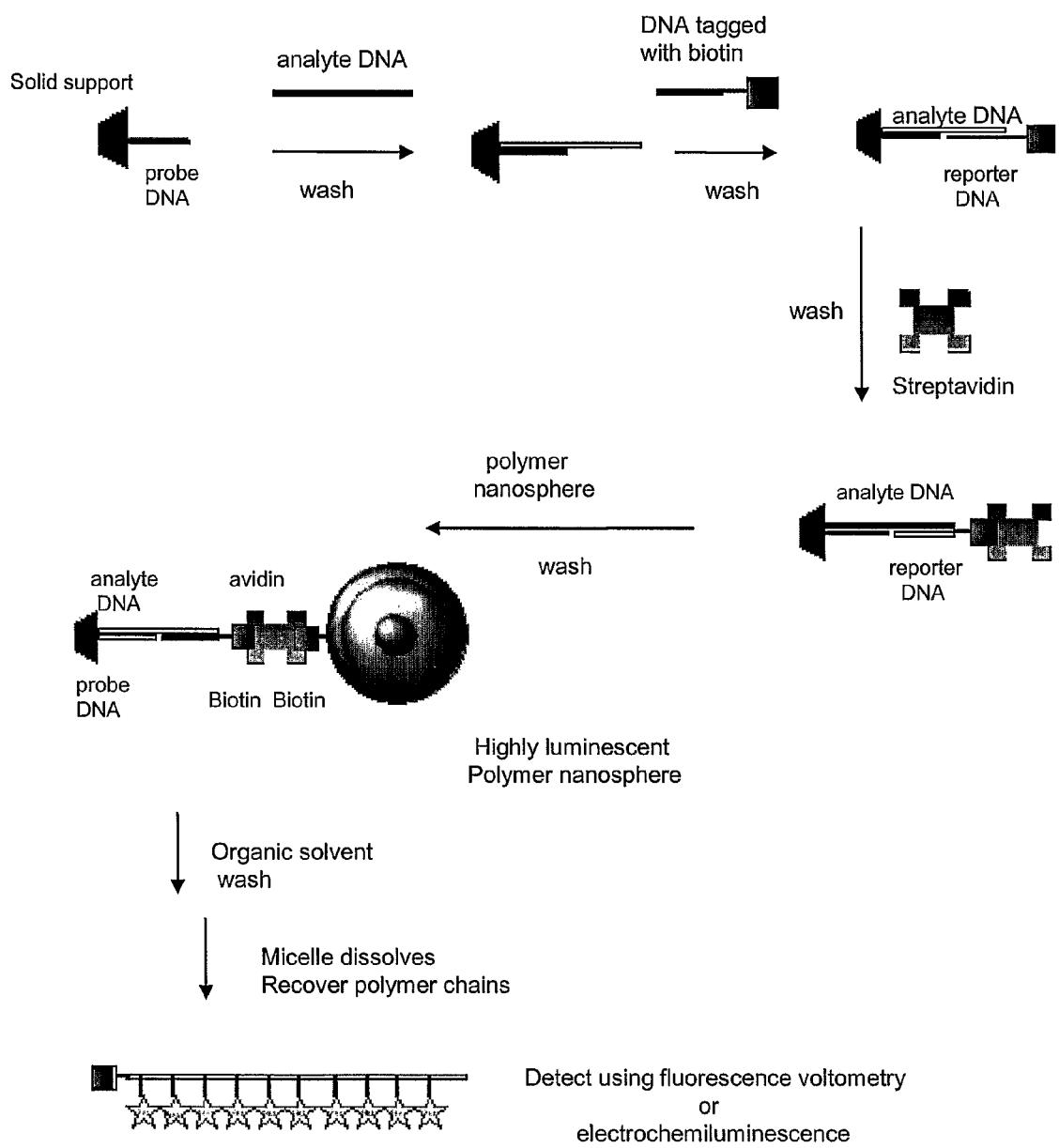
FIG. 5 is a schematic illustration of the use of a block copolymer in an assay in accordance with an embodiment of the present invention, providing for the detection of a targeted DNA sequence using fluorescence voltammetry or electrochemiluminescence.

The biological assay for the detection of a DNA/RNA sequence, using the block copolymers of the present invention, is illustrated in FIGS. 4 and 5. Hybridization of the analyte to a probe DNA molecule on a solid support is first carried out. The probe molecule is complementary to a portion of the analyte sequence. After washing, a biotinylated reporter DNA sequence complementary to the remainder of the analyte DNA sequence is added, followed by thorough washing. This essentially labels the analyte nucleic acid with a biotin molecule, given the analyte is complementary to the probe and reporter sequences. Stringent washes are carried out in both steps to remove any mismatched DNA.

The biotin-labeled, solid-supported analyte molecules are then incubated with streptavidin. Following washing, biotinylated polymer nanospheres are added resulting in the labeling of each analyte DNA with a polymeric nanosphere. When this assay is carried out on glass slides, the luminescence of the resulting DNA can be detected by confocal fluorescence microscopy. A similar detection assay can be designed for proteins, where the primary molecular recognition can be an antibody-antigen interaction.

Alternatively, the polymer nanospheres can be redissolved by adding an organic solvent such as DMF. The solvent washings can then be examined by solution fluorescence or electrochemical methods. A particularly attractive solution detection method is electrochemiluminescence (ECL). This relies on the oxidation of the ruthenium centers on an electrode followed by combination with an amine, which produces a very strong emission. Electrochemiluminescence (ECL) with $Ru(bpy)_3^{2+}$ as a reporter molecule has been widely used in medical diagnostics. The strong signal produced by this complex has allowed detection limits of $10^{-11}$ to $10^{-18}$ M of analyte to be reached using one ruthenium centre per analyte molecule. The polymer nanosphere-based assay of the present invention is expected to increase the detection sensitivity by a factor of approximately 10,000. In effect, each of the approximate 10,000 ruthenium centers that become associated with the analyte molecule acts as a catalyst to generate luminescence with many turnovers.

Micelle Formation and Transmission Electron Microscopy (TEM)

Distilled water was added dropwise to a stirred $CH_3CN$ solution of block copolymer 13 or 15 (the initial concentration is 5 mg/mL) until a final volume of 5 mL. The micelle solution was dialyzed several times against pure water over a period of 36 hours to remove the $CH_3CN$. The final concentration was then adjusted to 0.25 mg/mL. Samples were prepared by placing a drop of the solution onto TEM copper grids (400 mesh, carbon-coated, purchased from Electron Microscopy Sciences) to form a thin aqueous film. Any excess solution was blotted with a filter paper. The grids were air-dried for 12 h. The aggregates were then examined using a JEOL 2000FX electron microscope operated at 80 kV.

Synthesis of Macromonomer 6

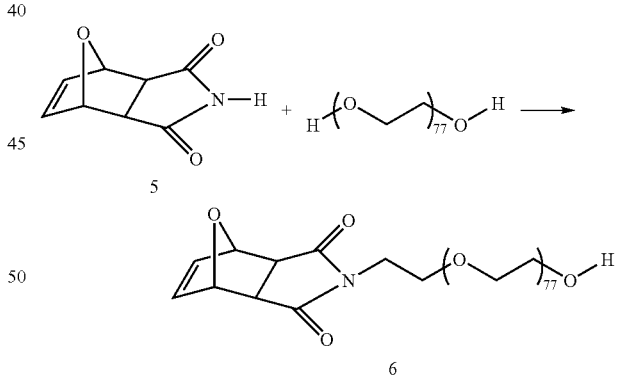

7-Oxanorbornene-5,6-exo-dicarboximide 5 (0.5 g, 3 mmol), polyethylene glycol (Mw=3400; 10.3 g, 3 mmol), and triphenylphosphine (0.786 g, 3 mmol) were dissolved in dry THF (100 mL) under a nitrogen atmosphere. The mixture was cooled to 0° C. followed by the addition of DEAD (0.531 g in THF) After the complete addition of the DEAD solution, the reaction mixture was allowed to warm up to room temperature and stirred for an additional 48 h. The solvent was removed under reduced pressure and the crude residue was purified by silica gel chromatography using methanol: $CH_2Cl_2$ as eluent to provide pure 6 (3 g). $^1$H NMR ($CDCl_3$): 2.84 (s, 2H), 3.64 (bs, 300H), 5.25 (s, 2H), 6.50 (s, 2H).

Synthesis of Biotin-Containing Monomer 9

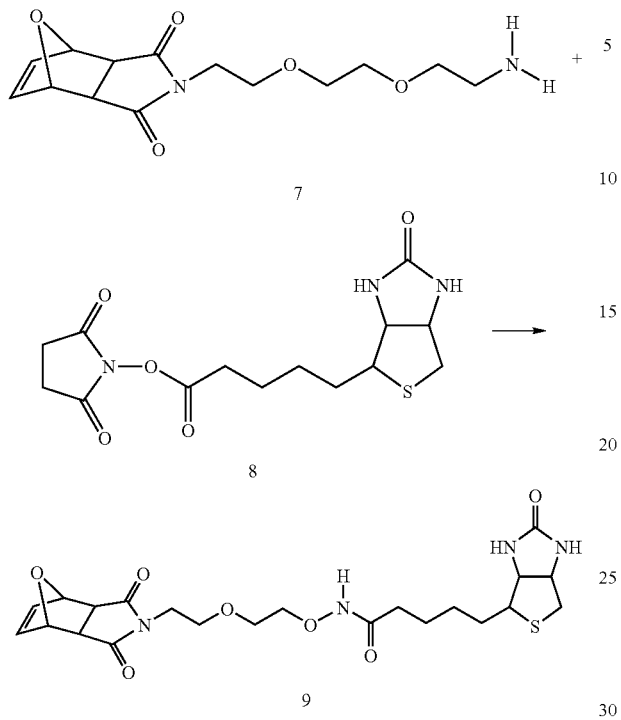

Compound 7 (1.1 g) and biotin-NHS ester 8 (1.4 g) were dissolved in CHCl₃ and isopropanol (2:1) (10 ml), followed by the addition of one drop of Et₃N. The mixture was stirred for 2 h at room temperature during which the cloudy mixture turned transparent. The solvent was removed under reduced pressure. Pure 9 (95%) was obtained by chromatography on silica gel using CH₂Cl₂:methanol (95:5) as eluent. ¹H NMR (CD₃Cl): 1.4-1.6 (m, 6H), 2.26 (t, 2H), 2.70 (d, 2H), 2.87 (dd and s, 3H), 3.16 (m, 1H), 3.38 (m, 3H), 3.41-3.68 (m, 12H), 4.29 (m, 1H), 4.49 (m, 1H), 5.23 (m, 2H), 5.69 (s, 1H), 6.50 (s, 2H), 6.58 (s, 1H), 6.76 (t, 1H).

Synthesis of Monomer 10

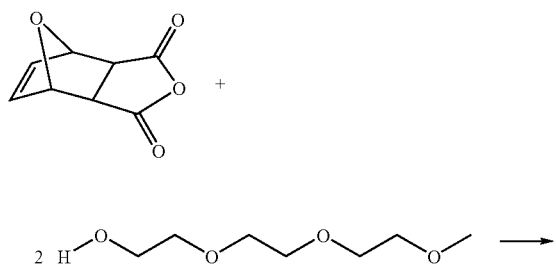

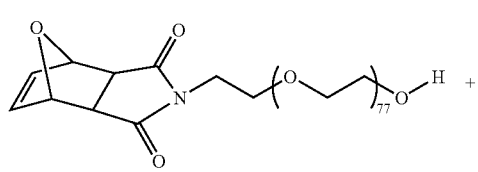

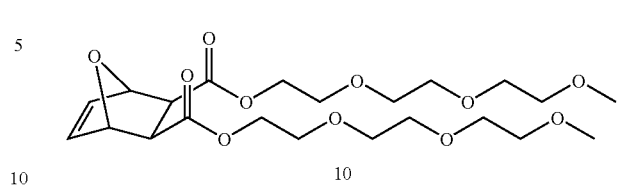

Anhydride (1.66 g, 10 mmol), triethylene glycol monomethyl ether (3.6 g, 22 mmol), DMAP (0.54 g, 4 mmol) and 2-chloro-1-methyl-pyridium iodide (3.26 g, 12 mmol) were weighted and transferred to a dry flask. CH₂Cl₂ (7 ml) was added followed by the addition of triethylamine (6.85 ml). The mixture was refluxed for 2 days under a nitrogen atmosphere. After pouring the mixture into water (50 ml), CH₂Cl₂ (50 mL) was added and the organic phase separated and subsequently washed with water, dilute HCl (pH=5) and brine. Pure 10 (90%) was obtained following chromatography on silica gel using CH₂Cl₂:methanol (30:1) as eluent. ¹H NMR ((D₂O): 2.97 (s, 2H), 3.26 (s, 6H), 3.48-3.66 (m, 20H), 4.08-4.28 (m, 4H), 5.20 (s, 2H), 6.44 (s, 2H).

Synthesis of Monomer 11

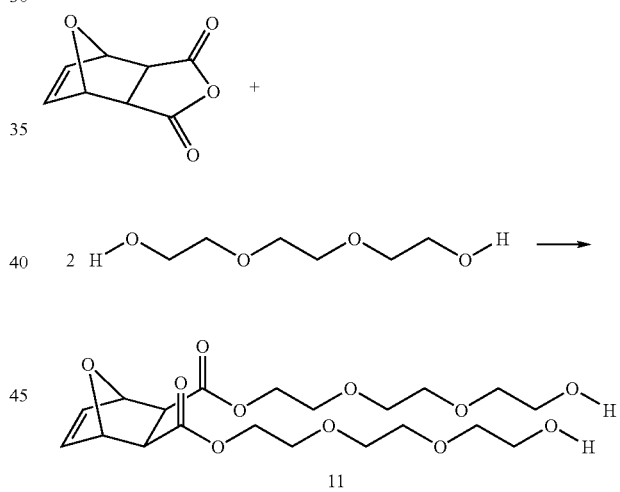

The procedure as described hereinabove above for the synthesis of monomer 10 was used for the preparation of monomer 11 with the exception that a 10-fold excess of triethylene glycol was used. ¹H NMR (CDCl₃): 2.86 (s, 2H), 3.60-3.74 (m, 20H), 4.30 (m, 4H), 5.30 (s, 2H), 6.45 (s, 2H).

Synthesis of Biotin-Containing Macromonomer 13

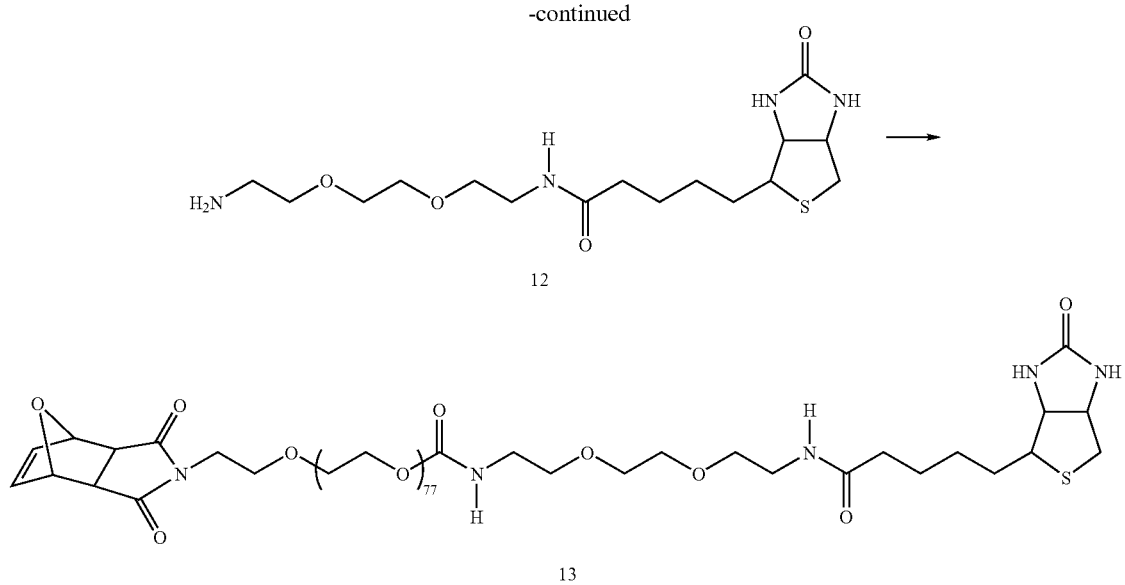

A dry DMF solution of macromonomer 6 (0.7 g) was added dropwise to a dry DMF solution of carbonyldiimidazole (36 mg) at 0° C. After 1 h of stirring at 0° C., a dry DMF solution of N-(8-Amino-3,6-dioxaoctayl)biotinamide 12 (0.1 g) was added and the mixture was stirred at room temperature for 1 h. The solvent was subsequently removed under reduced pressure. Pure 13 was obtained by chromatography on silica gel.

Synthesis of Biotin-Quencher 16 for ROMP

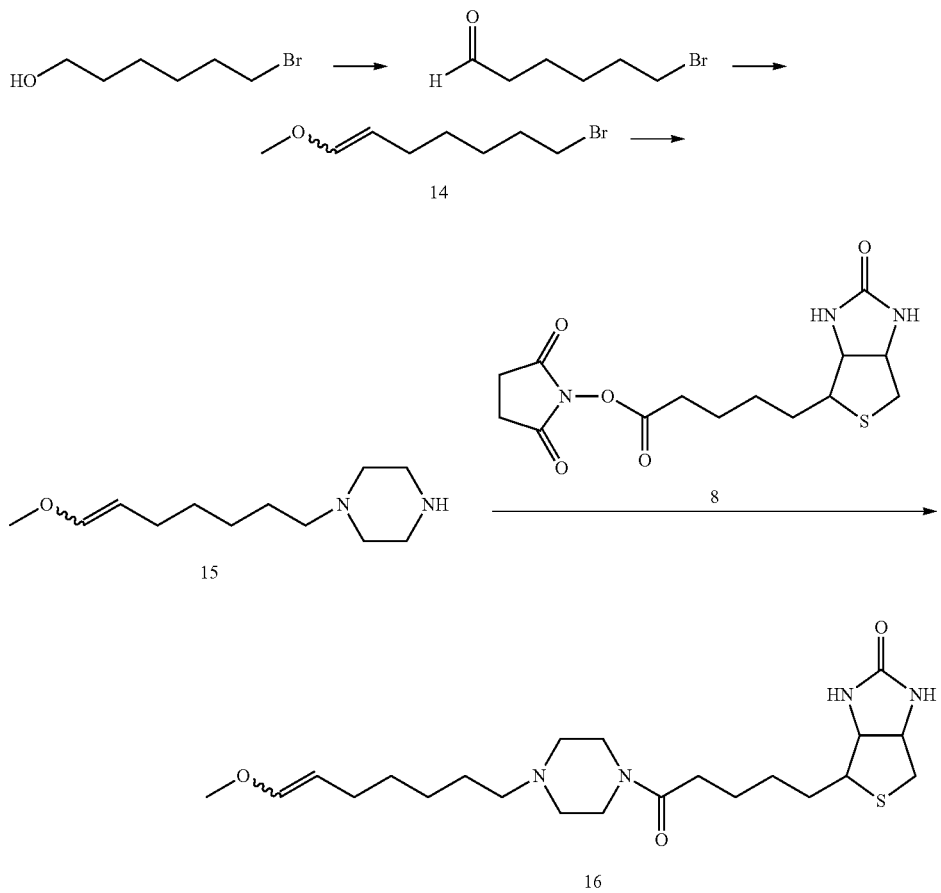

Potassium tert-butoxide (1M in THF, 3.35 mL 3.35 mmol) was added to a suspension of (methoxymethyl)triphenylphosphonium chloride (1.15 g, 3.35 mmol) in dry THF at 0° C. The dark red solution was stirred at 0° C. under $N_2$ for 5 min. The solution was then transferred to a flask containing 6-bromo-1-hexanal (0.6 g; 3.35 mmol) dissolved in THF (10 ml). The orange color rapidly disappeared, and a grey precipitate formed. The reaction mixture was quenched with saturated aqueous NaCl (20 mL) and extracted with $CH_2Cl_2$ (3×15 mL). The combined organic extracts were washed with water and brine, and dried over $Na_2SO_4$. After removing the solvent, crude 14 was obtained (56%) which was used for next step without further purification.

Piperazine (0.86 g, 10 mmol) and compound 14 (0.4 g) were dissolved in dry $CH_3CN$ (10 mL) followed by the addition of $K_2CO_3$ (0.4 g). Following overnight refluxing and cooling to room temperature, the mixture was filtered and the solvent as well as excess piperazine removed under vacuum. Pure 15 was obtained following chromatography on alumina using $CH_2Cl_2$:methanol (100:5) as eluant. $^1$H NMR (δ ppm): 1.32 (4H, m), 1.49 (2H, m), 1.93 (2H, q, J=6.9 Hz), 2.30 (2H, t, J=7.8 Hz), 2.42 (bs, 4H), 2.91 (4H, t, J=5.0 Hz), 3.52 (2H, s, trans-OCH3), 3.57 (1H, s, cis-OCH3), 4.32 (0.33H, dxt, J=7.1×7.0 Hz, cis-OCH=CH), 4.71 (0.66H, dxt, J=12.3×7.5 Hz, trans-OCH=CH), 5.85 (0.33H, dxt, J=6.2×1.5 Hz, cis-OCH=CH), 6.26 (0.66, d, J=11.1 Hz, trans-OCH=CH); $^{13}$C NMR (δ ppm): 24.14, 26.83, 27.31, 27.58, 27.96, 30.08, 31.05, 46.26, 54.70, 56.21, 59.66, 103.23, 107.08, 146.21, 147.16.

Compound 15 (200 mg, 0.94 mmol) and biotinyl-N-hydroxysuccinimide 8 (350 mg, 1.0 mmol) were dissolved in $CHCl_3$/2-propanol (2:1) (20 mL) followed by the addition of triethylamine (200 mL). Slight warming and ultrasonication provided a clear solution. The solution was subsequently stirred for 1 h at room temperature followed by the removal of the solvents under reduced pressure. Pure 16 (83%) was obtained by chromatography on alumina using $CH_2Cl_2$:methanol (98:2) as eluant. $^1$H NMR (δ ppm): 1.33 (4H, m), 1.49 (4H, m), 1.68 (4H, m), 1.93 (2H, m), 2.09 (1.2H, trans-OCH=CHCH2), 2.38 (8H, —CH2N(CH2-)$_2$), 2.73 (1H, bd, J=10.8 Hz, SCH2), 2.91 (1H, dd, J=12.9×4.8 Hz, SCH2), 3.16 (1H, m, CHS), 3.20-3.60 (7H, m, cis- and trans-OCH3, CON(CH2)$_2$), 4.31 (1.33H, m, NCH and cis-OCH=CH), 4.5 (1H, m, NCH), 4.71 (0.66H, dxt, J=12.3×7.5 Hz, trans-OCH=CH), 5.2 (1H, NH), 5.8 (1H, NH), 5.85 (0.33H, dxt, J=6.2×1.5 Hz, cis-OCH=CH), 6.26 (0.66, d, J=11.1 Hz, trans-OCH=CH); $^{13}$C NMR (δ ppm): 24.12, 25.44, 27.02, 27.20, 27.47, 27.96, 28.64, 28.69, 30.04, 31.01, 33.00, 40.91, 41.89, 45.97, 53.23, 53.84, 55.65, 56.23, 58.89, 60.44, 62.11, 103.17, 106.99, 146.27, 147.21, 163.53, 171.42.

Synthesis of Triblock Copolymer 20

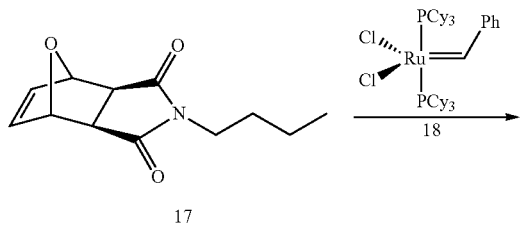

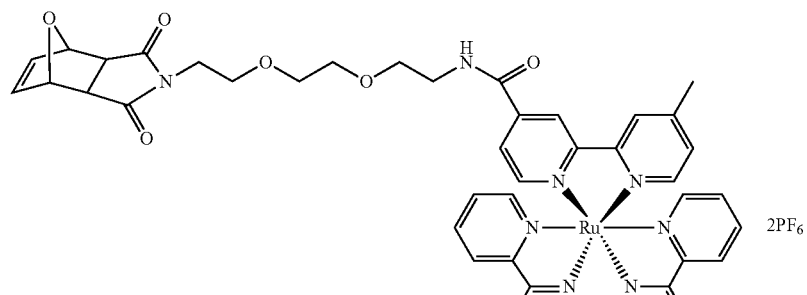

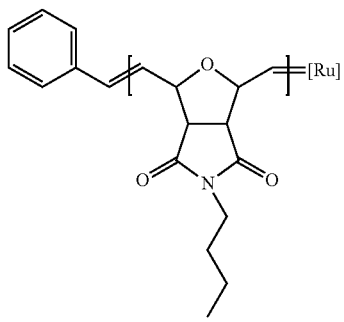

-continued
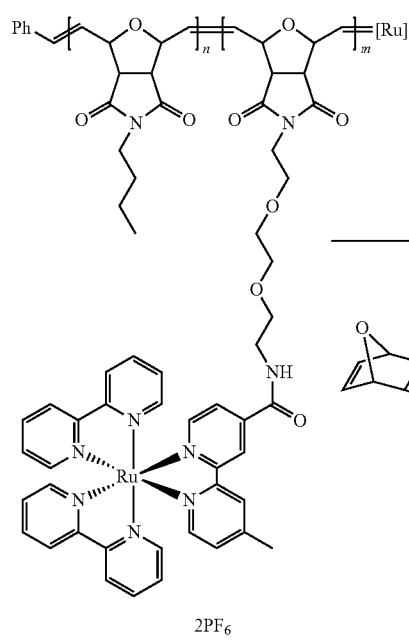
23
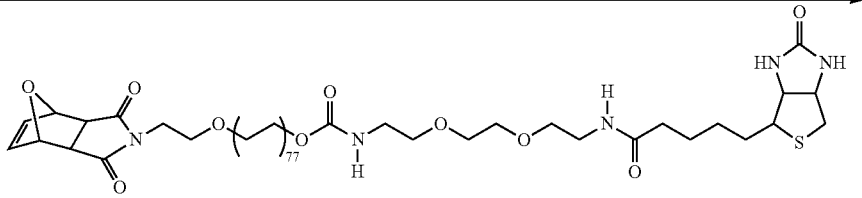
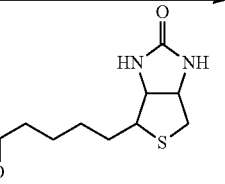
13
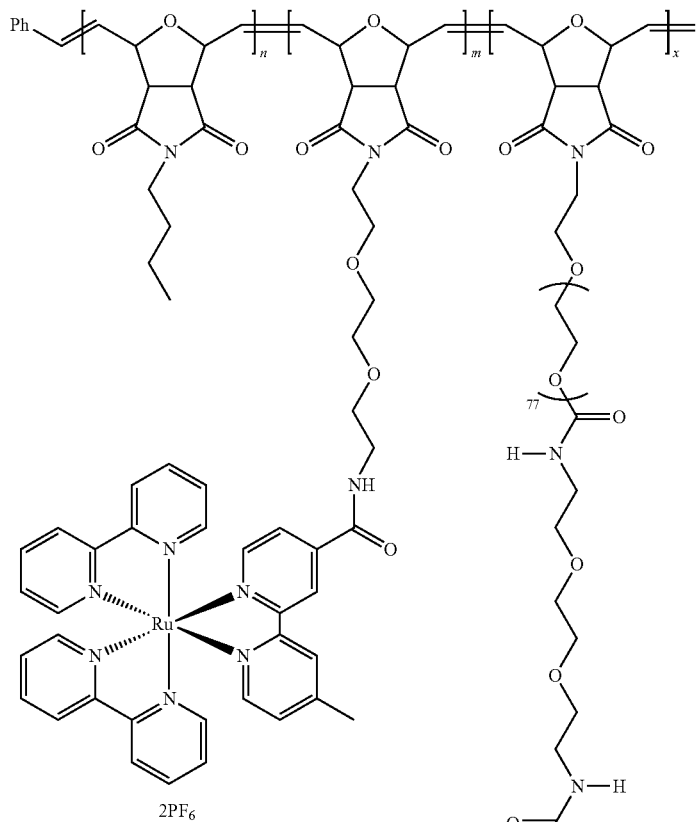

A solution of monomer 17 (10 mg) in $d_6$-acetone (5 mL) was added to a solution of catalyst 18 (2 mg) in $d_6$-acetone (0.2 mL) and the reaction mixture stirred at room temperature. After the complete consumption of monomer 17 (as monitored by $^1$H NMR), a solution of monomer 19 (20 mg) in $d_6$-acetone (1 mL) was added. After the complete consumption of monomer 19 (as monitored by $^1$H NMR), a solution of biotinylated macromonomer 13 (80 mg) in $d_6$-acetone (2 mL) was added. Following the complete consumption of monomer 13 (as monitored by $^1$H NMR), the reaction mixture was quenched by the addition of ethyl vinyl ether. Copolymer 20 was obtained following precipitation from ether. $^1$H NMR ($d_6$-acetone): 0.98 (bs, 3H), 1.3 (bs, 2H), 1.54 (bs, 2H), 2.54 (s, 0.9H), 3.3-3.8 (300H), 4.45 (cis-H), 5.08 (cis-H), 5.83 (trans-H), 6.04 (trans-H), 7.2-9.2 (bipyridine-H).

Synthesis of Diblock Copolymers 13, 15 and 21, 22.

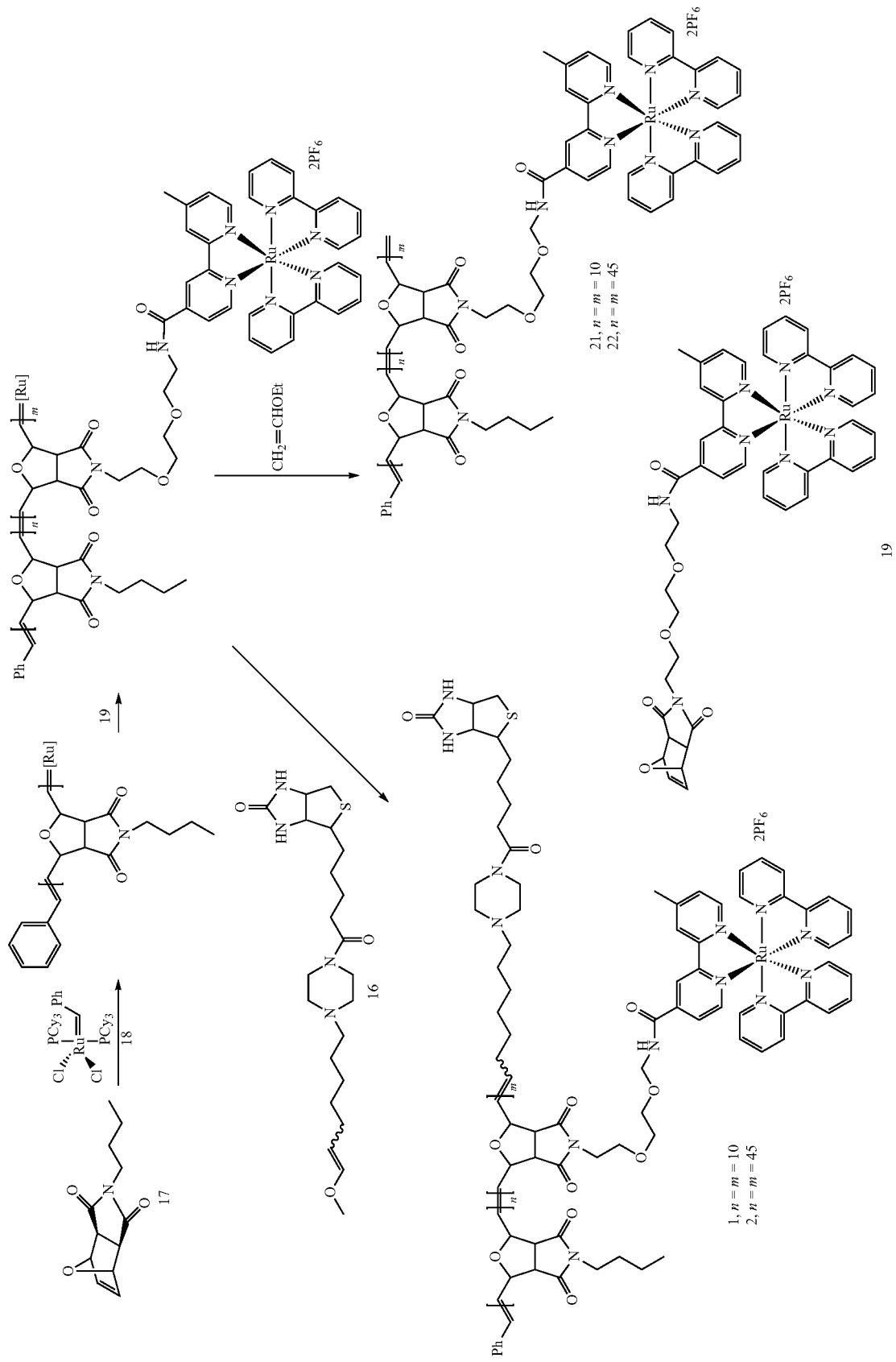

A solution of monomer 17 (2.0 mg, 0.009 mmol) in d$_6$-acetone (0.5 mL) was added to a solution of catalyst 18 (0.0003 mmol) in CD$_2$Cl$_2$ (0.2 mL) and the reaction mixture stirred at room temperature. After the complete consumption of monomer 17 (as monitored by $^1$H NMR), a solution of monomer 19 (10.7 mg, 0.009 mmol) in d$_6$-acetone (1 mL) was added. After the complete consumption of monomer 19 (as monitored by $^1$H NMR), the reaction mixture was divided into two portions. A first portion was added to a d$_6$-acetone solution of excess biotin quencher 16 (30 equiv), and the reaction mixture stirred for 3 h. Copolymers 13 and 15 were obtained following precipitation from ether. The second portion was quenched by the addition of ethyl vinyl ether. Copolymers 21 and 22 were obtained following precipitation from ether.

Copolymer 1: $^1$H NMR CD$_3$CN (δ ppm): 0.94 (br, 3H), 1.31 (br, 2H), 1.54 (br, 2H), 2.53 (br, 3H), 2.8-3.0 (0.2H, biotin SCH2), 3.1-3.2 (0.4H), 3.2-3.6 (br, 18H), 4.2-4.88 (br, 4H), 5.5-6.1 (br, 4H), 7.28 (br, 1H), 7.40 (br, 4H), 7.60 (br, 1H), 7.66 (br, 1H), 7.75 (br, 4H), 7.86 (br, 1H), 8.06 (br, 4H), 8.50 (br, 4H), 8.60 (br, 1H), 8.90 (br, 1H).

Copolymer 2: $^1$H NMR CD$_3$CN (δ ppm): 0.94 (br, 3H), 1.31 (br, 2H), 1.54 (br, 2H), 2.53 (br, 3H), 3.2-3.6 (br, 18H), 4.2-4.88 (br, 4H), 5.5-6.1 (br, 4H), 7.28 (br, 1H), 7.40 (br, 4H), 7.60 (br, 1H), 7.66 (br, 1H), 7.75 (br, 4H), 7.86 (br, 1H), 8.06 (br, 4H), 8.50 (br, 4H), 8.60 (br, 1H), 8.90 (br, 1H).

Copolymer 21: $^1$H NMR CD$_3$CN (δ ppm): 0.92 (br, 3H), 1.33 (br, 2H), 1.54 (br, 2H), 2.53 (br, 3H), 3.2-3.6 (br, 18H), 4.2-4.5 (br, 2.6H), 4.88 (br, 1.4H), 5.5-6.1 (br, 4H), 7.28 (br, 1H), 7.40 (br, 4H), 7.60 (br, 1H), 7.66 (br, 1H), 7.75 (br, 4H), 7.86 (br, 1H), 8.06 (br, 4H), 8.50 (br, 5H), 8.90 (br, 1H).

Copolymer 22: $^1$H NMR CD$_3$CN (δ ppm): 0.92 (br, 3H), 1.33 (br, 2H), 1.54 (br, 2H), 2.53 (br, 3H), 3.2-3.6 (br, 18H), 4.2-4.5 (br, 2.6H), 4.88 (br, 1.4H), 5.5-6.1 (br, 4H), 7.28 (br, 1H), 7.40 (br, 4H), 7.60 (br, 1H), 7.66 (br, 1H), 7.75 (br, 4H), 7.86 (br, 1H), 8.06 (br, 4H), 8.50 (br, 5H), 8.90 (br, 1H).

Synthesis of Tetrablock Copolymers 23 and 24

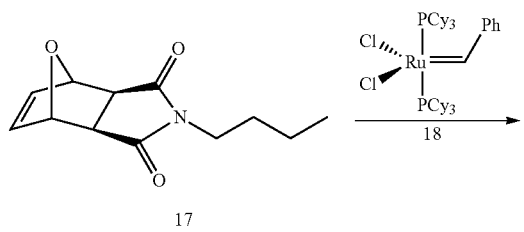

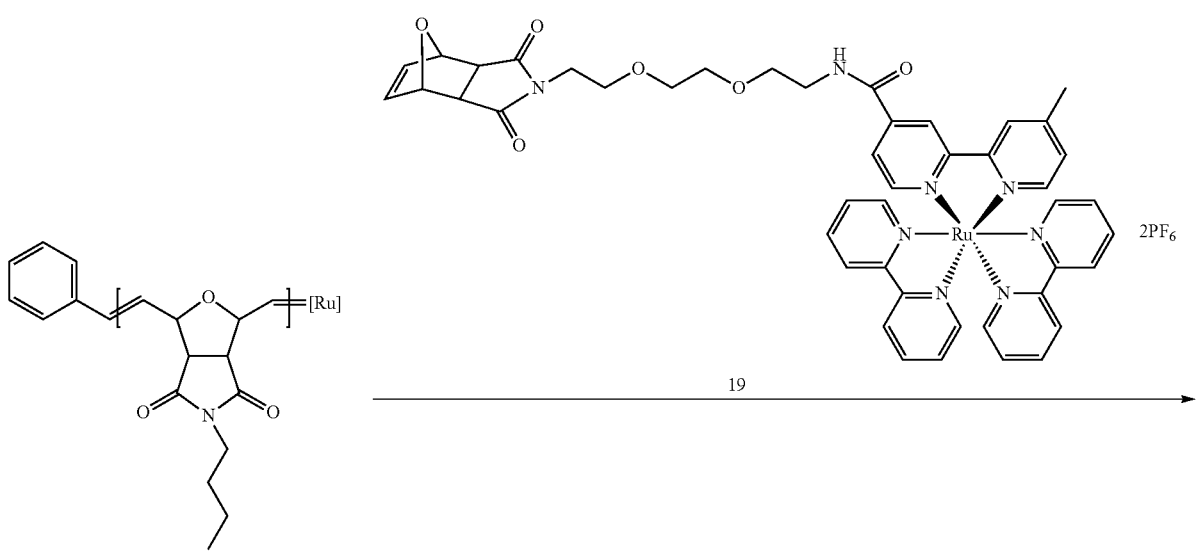

31
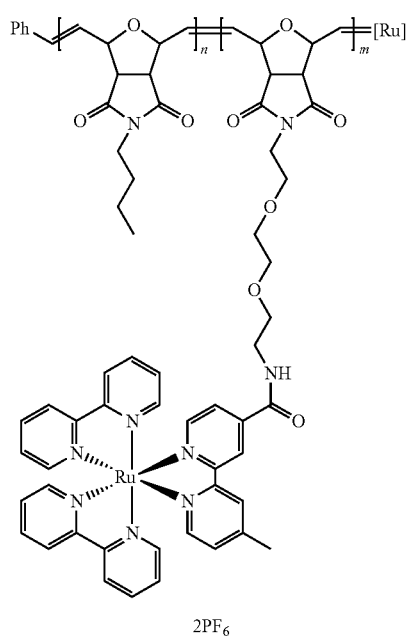
32
-continued
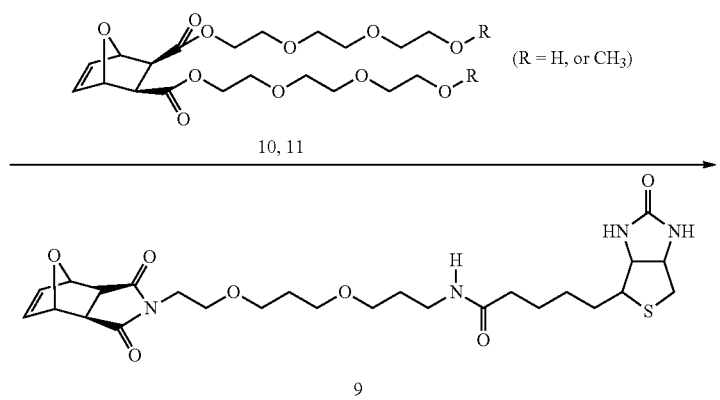
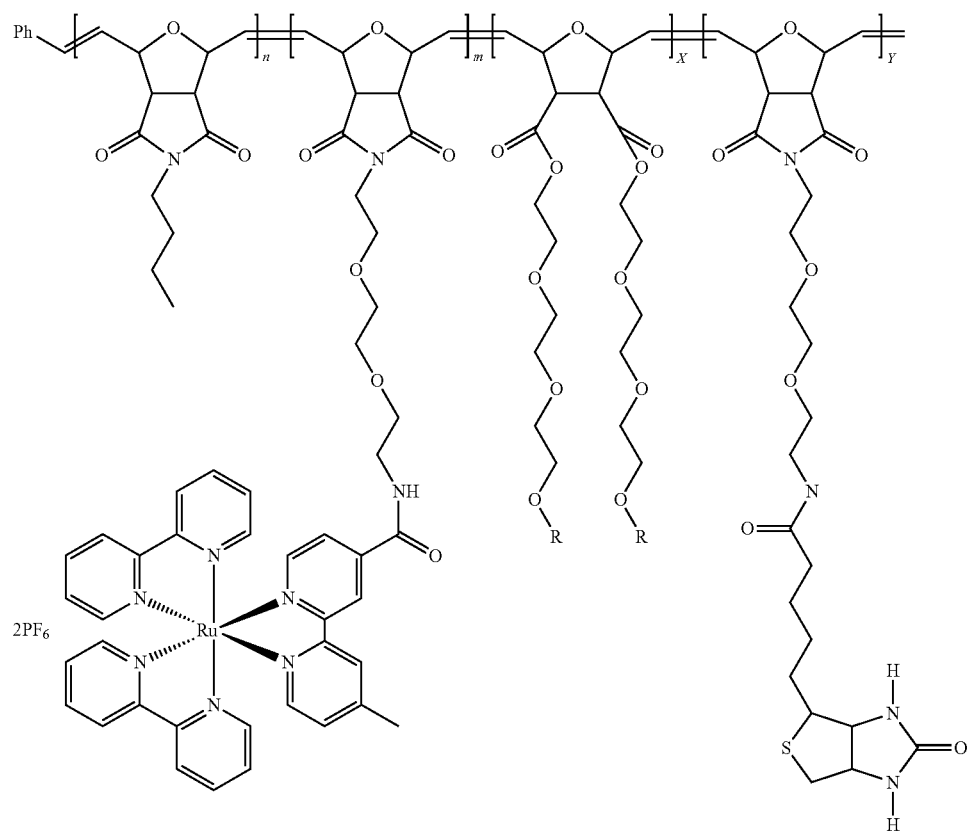
23 R = CH₃
24 R = H

A solution of monomer 17 (3.7 mg) in d₆-acetone (0.5 mL) was added to a solution of catalyst 18 (0.4 mg) in d₆-acetone (0.2 mL) and the reaction mixture stirred at room temperature. After the complete consumption of monomer 17 (as monitored by ¹H NMR), a solution of monomer 19 (20 mg) in d₆-acetone (1 mL) was added. After the complete consumption of monomer 19 (as monitored by ¹H NMR), a solution of monomer 10 or 11 (7.8 mg) in d₆-acetone (1 mL) was added. After the complete consumption of monomer 10 or 11 (as monitored by ¹H NMR), a solution of monomer 9 (0.7 mg) in d₆-acetone (1 mL) was added. Following the complete consumption of monomer 9 (as monitored by ¹H NMR), the reaction mixture was quenched by the addition of ethyl vinyl ether. Copolymers 23 and 24 were obtained following precipitation from ether. ¹H NMR (CD₃CN); 23: 0.95 (bs, 3H), 1.37 (bs, 2H), 1.57 (bs, 2H), 2.55 (s, 3H), 3.1-3.7 (32H), 4.1-5.1 (cis-H), 5.6-6.1 (trans-H), 7.2-8.8 (22H, Bipyridine-H); 24; 0.95 (bs, 3H), 1.37 (bs, 2H), 1.57 (bs, 2H), 2.55 (s, 3H), 3.1-3.7 (28H), 4.1-5.1 (cis-H), 5.6-6.1 (trans-H), 7.2-8.8 (22H, Bipyridine-H).

Synthesis of Tetrablock Copolymer 3

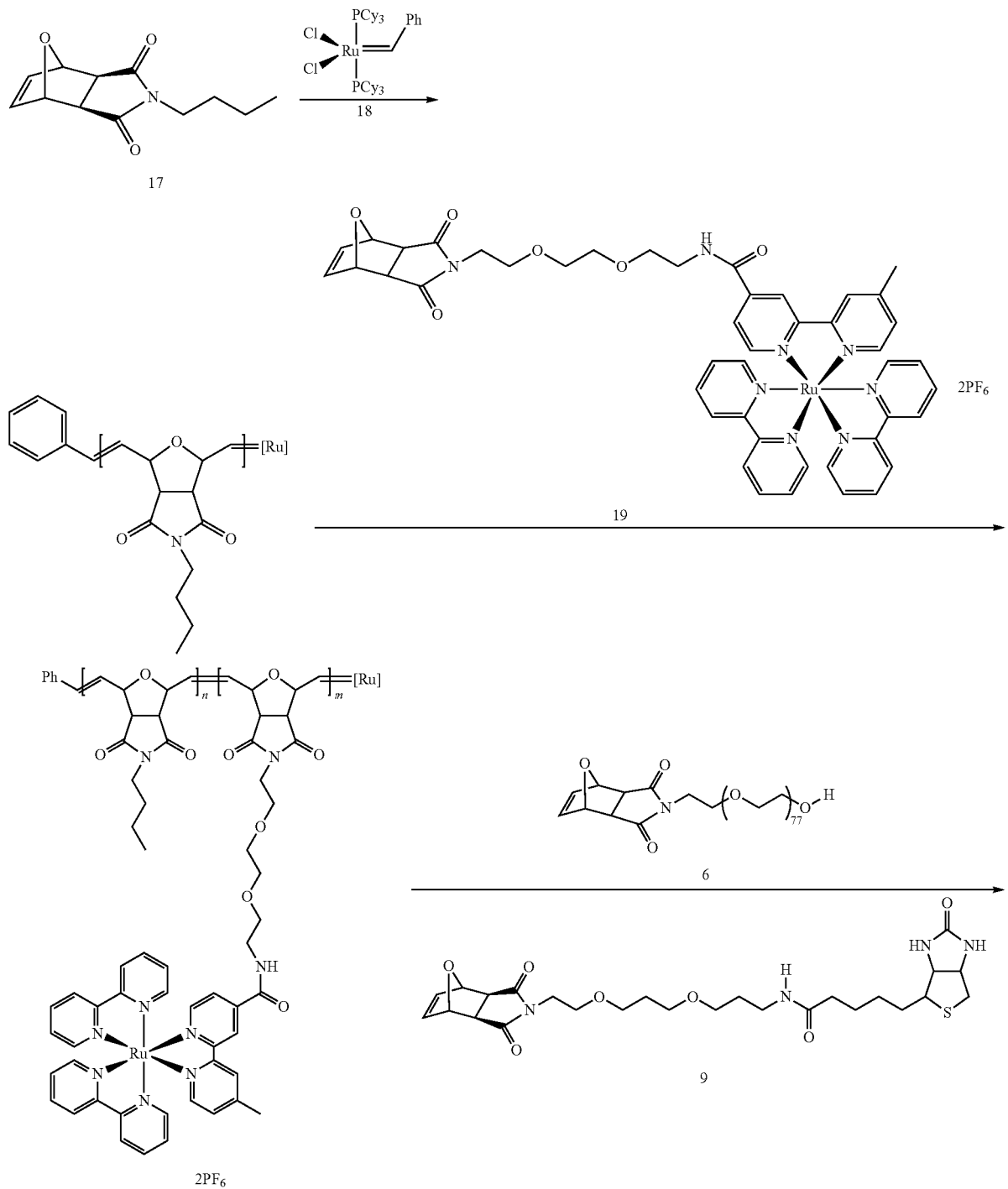

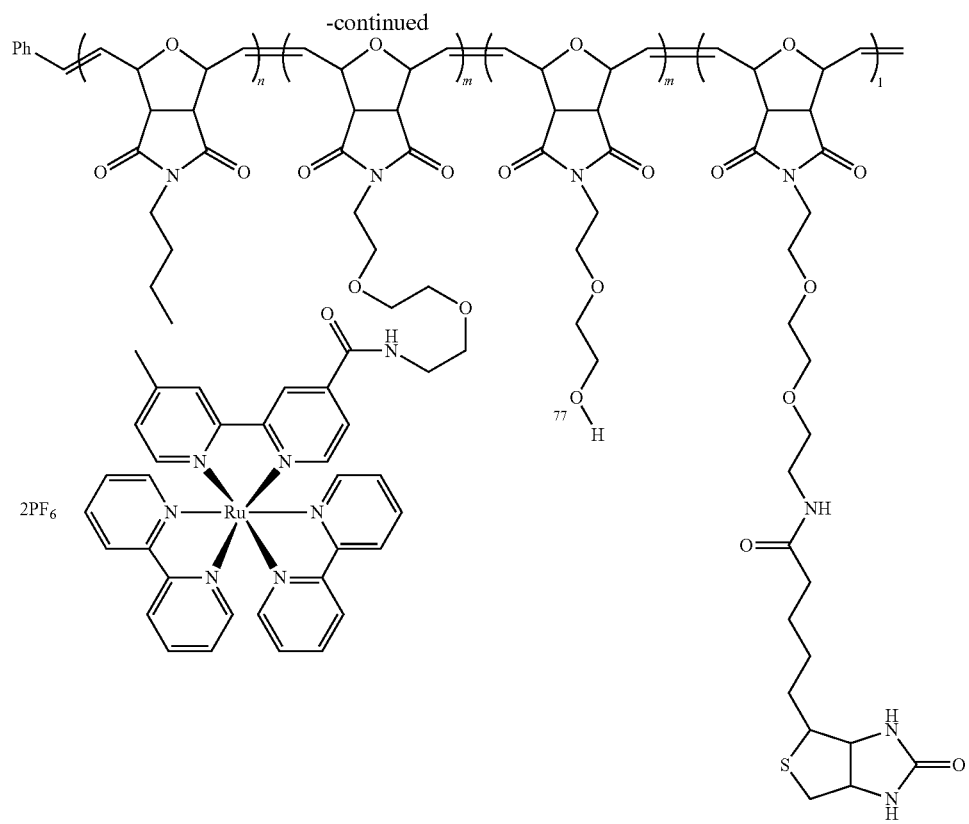

A solution of monomer 17 (10 mg) in $d_6$-acetone (0.5 mL) was added to a solution of catalyst 18 (2.0 mg) in $d_6$-acetone (0.2 mL) and the reaction mixture stirred at room temperature. After the complete consumption of monomer 17 (as monitored by $^1$H NMR), a solution of monomer 19 (20 mg) in $d_6$-acetone (1 mL) was added. After the complete consumption of monomer 19 (as monitored by $^1$H NMR), a solution of monomer 6 (80 mg) in $d_6$-acetone (1 mL) was added. After the complete consumption of monomer 6 (as monitored by $^1$H NMR), a solution of monomer 9 (0.7 mg) in $d_6$-acetone (1 mL) was added. Following the complete consumption of monomer 9 (as monitored by $^1$H NMR), the reaction mixture was quenched by the addition of ethyl vinyl ether. Copolymer 3 was obtained following precipitation from ether. $^1$H NMR ($d_6$-acetone): 0.98 (bs, 3H), 1.3 (bs, 2H), 1.54 (bs, 2H), 2.54 (s, 0.9H), 3.3-3.8 (300H), 4.45 (cis-H), 5.08 (cis-H), 5.83 (trans-H), 6.04 (trans-H), 7.2-9.2 (bipyridine-H).

Synthesis of Bipyridinyl Ligand 29

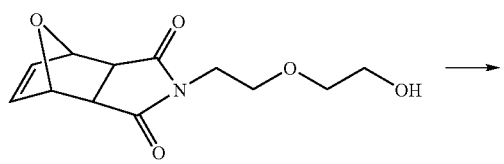

26

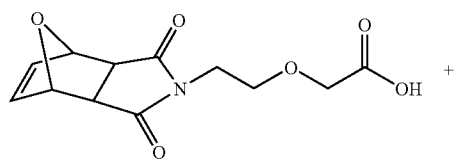

27

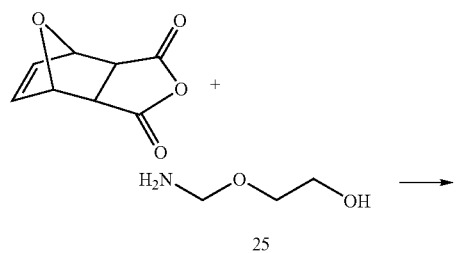

25

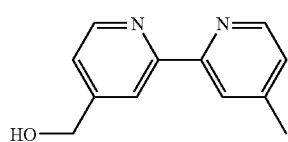

28

-continued

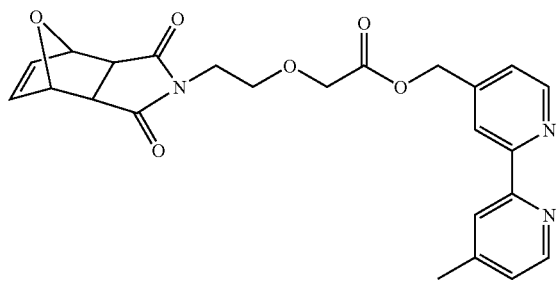

29

Anhydride (5.0 g) and compound 25 (15.0 g) were mixed and stirred at 80° C. for 2 h. Following cooling to room temperature, the mixture was dissolved in CH$_2$Cl$_2$ (200 mL) and was washed with brine. The solvent was removed under reduced pressure to yield product 26 (5.0 g) which was subsequently dissolved in acetone (100 mL) followed by the dropwise addition of Jones reagent at room temperature. The mixture was stirred at room temperature until the starting material was completely consumed (as monitored by TLC: CH$_2$Cl$_2$:methanol; 20:1). The clear solution was poured into water (200 ml) and extracted with ethyl acetate (50 ml). The combined extracts were subsequently washed with water and brine followed by drying over Mg$_2$SO$_4$ to yield product 27 (0.9 g).

Product 27 and compound 28 (1:1 ratio) were dissolved in CH$_2$Cl$_2$ (100 ml) and one equivalent of DCC was added. The reaction mixture was then sonicated for 10 h at room temperature. Removal of the solvent, and purification by chromatography on silica gel yielded product 29. $^1$H NMR (CDCl$_3$) 2.43 (s, 3H), 2.84 (s, 2H), 3.72 (s, 4H), 4.17 (s, 2H), 5.2 (s, 2H), 7.14 (d, 1H), 7.25 (d, 1H), 8.22 (s, 1H), 8.33 (s, 1H), 8.50 (d, 1H), 8.64 (d, 1H).

Synthesis of Bipyridinyl Ligand 31

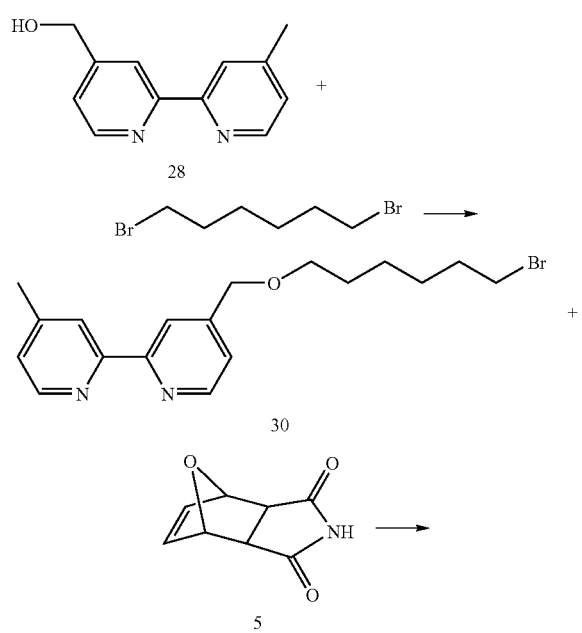

-continued

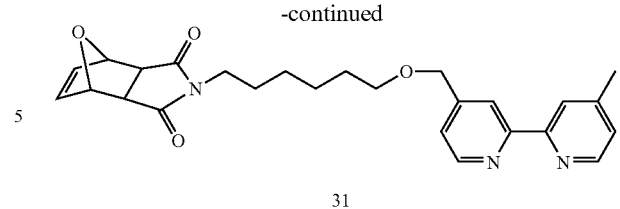

31

Compound 28 (0.1 g, 0.5 mmol), 1,6-dibromohexane (5 mmol) and KOH (0.03 g) were heated in refluxing toluene (10 ml) for 21 h. After cooling to room temperature, water (20 ml) and dichloromethane were added. The organic phase was subsequently separated and washed with water and brine followed by drying. Pure 30 (90 mg) was obtained following chromatography on silica gel. $^1$H NMR (CDCl$_3$): 1.46 (m, 4H), 1.66 (m, 2H), 1.87 (m, 2H), 3.37 (t, 2H), 3.54 (t, 3H), 7.11 (d, 1H), 7.31 (d, 1H), 8.21 (s, 1H), 8.31 (s, 1H), 8.51 (d, 1H), 8.63 (d, 1H). Compound 30 (0.1 g) was dissolved in dry DMF (5 mL) and 5 (0.09 g) was added. The reaction mixture was stirred at room temperature for 14 h under a nitrogen atmosphere. The crude mixture was poured into water (20 mL) was extracted with chloroform. The organic phase was washed with water and brine. Pure 31 was obtained following chromatography on silica gel. $^1$H NMR (CDCl$_3$): 1.2-1.7 (8H), 2.5 (s, 3H), 2.81 (s, 2H), 3.5 (m, 4H), 4.61 (s, 2H), 5.25 (s, 2H), 6.49 (s, 2H), 7.22 (d, 1H), 7.42 (d, 1H), 8.36 (s, 1H), 8.40 (s, 1H), 8.58 (d, 1H), 8.68 (d, 1H).

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES (1) Staffilani, M.; Hoss, E.; Giesen, U.; Schneider, E.; Josel, H.-P.; De Cola, L. *Inorg. Chem.* 2003, 42, 7789. Zhou, M.; Roovers, J. *Macromolecules* 2001, 34, 244. Zhou, M.; Roovers, J.; Robertson, G. P.; Grover, C. P. *Anal. Chem.* 2003, 76, 6708.

(2) Miao, W.; Bard, A. *Anal. Chem.* 2004, 76, 5379.

(3) Kurner, J. M.; Klimant, I.; Krause, C.; Preu, H.; Kunz, W.; Wolfbeis, O, S. *Bioconjugate Chem.* 2001, 12, 883.

(4) Santra, S.; Zhang, P.; Wang, K.; Tapec, R.; Tan, W. *Anal. Chem.* 2001, 73, 4988. Wang, L.; Yang, C.; Tan, W. *Nano Letters* 2005, 5, 37. Rossi, L., *Shi, L.; Quina, F. H.; Rosenzweig, Z. *Langmuir* 2003, 21, 4277.

(5) Nam, J.-M.; Stoeva, S. I.; Mirkin, C. A. *J. Am. Chem. Soc.* 2004, 126, 5932.

(6) Juris, A.; Balzani, V.; Barigelletti, F.; Campagna, S.; Belser, P.; Von Zelewsky, A. *Coord. Chem. Rev.* 1988, 84, 85. Kaes, C.; Katz, A.; Hosseini, M. W. *Chem. Rev.* 2000, 100, 3553. Yu, S. C.; Hou, S.; Chan, W. K; Liu, Y.; Li, Y.; Schanze, K. S. *J. Photochem. Photobiol., C: Photochem. Rev.* 2002, 3, 1-23.

(7) Carlise, J. R.; Weck, M. *J. Polym. Sci., Part A: Polym. Chem.* 2004, 42, 2973. Pautzsch, T.; Blankenburg, L.; Klemm, E. *J. Polym. Sci., Part A: Polym. Chem.* 2004, 42, 722. Yu, S. C.; Hou, S.; Chan, W. K. *Macromolecules* 2000, 33, 3259 and references cited therein.

(8) Sykora, M.; Maxwell, K. A.; Desimone, J. M.; Meyer, T. J. *Proc. Nat. Acad. Sci. U.S.A.* 2000, 97, 7687. Friesen, D. A.; Kajita, T.; Danielson, E.; Meyer, T. J. *Inorg. Chem.* 1998, 37, 2756. Dupray, L. M.; Meyer T. J. *Inorg. Chem.* 1996, 35, 6299. Ogoshi, T.; Itoh, H.; Kim, K, -M.; Chujo, Y. *Macromolecules* 2002, 35, 334.

(9) Elliott, C. M.; Baldy, C. J.; Nuwaysir, L. M.; Wilkins, C. L. *Inorg. Chem.* 1990, 29, 389. Pitt, C. G.; Bao, Y.; Seltzman, H. H. *J. Polym. Sci., Polym. Leff. Ed.* 1986, 24, 13. Cho, Y.-S.; Lee, J.-S. *Macromol. Chem. Phys.* 2002, 203, 2495.

(10) Meier, M. A. R.; Marin, V.; Schubert, U.S. *J. Polym. Sci., Part A: Polym. Chem.* 2003, 41, 3954. Marin, V.; Holder, E.; Schubert, U.S. *J. Polym. Sci., Part A: Polym. Chem.* 2004, 42, 374. Lohmeijer, B. G. G.; Schubert U.S. *Angew. Chem., Int. Ed.* 2002, 41, 3825, Gohy, J. F. B; Lohmeijer, G. G.; Schubert, U.S. *Chem. Eur. J.* 2003, 9, 3472.

(11) Knapp, R.; Kelch, S.; Schmeiz, O.; Rehahn, M. *Macromol. Symp.* 2003, 204, 267. Kelch, S.; Rehahn, M. *Macromolecules* 1999, 32, 5818. Hjelm, J.; Constable, E. C.; Figgemeier, E.; Hagfeld, A.; Handel, R.; Housecroft, C. E.; Mukhtar, E.; Schofield, E. *Chem. Commun.* 2002, 284.

(12) Kimura, M.; Horai, T.; Hanabusa, K.; Shirai, H. *Adv. Mater.* 1998, 10, 459.

(13) Gould, S.; Strouse, G. F.; Meyer, T. J.; Sullivan, B. P. *Inorg. Chem.* 1991, 30, 2942. Eaves, J. G.; Munro, H. S.; Parker, D. J. *Chem. Soc., Chem. Commun.* 1985, 684. Aranyo, S. V.; Hjelm, J.; Hagfeldt, A.; Grennberg. H. J. *Chem. Soc., Dalton Trans.* 2001, 1319. Wang, J.; Keene, F. R. *J. Electroanal. Chem.* 1996, 405, 71.

(14) Smith, A. P.; Fraser, C. L. *Macromolecules* 2003, 36, 5520. Peter, K.; Thelakkat, M. *Macromolecules* 2003, 36, 1179.

(15) Storrier, G. D.; Takada, K.; Abruna, H. D. *Langmuir* 1999, 15, 872. Murfee H. J.; Thoms, T. P. S.; Greaves, J.; Hong, B. *Inorg. Chem.* 2000, 39, 5209. Newkome, G. R.; Patri, A. K.; Godinez, L. A. *Chem. Eur. J.* 1999, 5, 1445. Zhou, M.; Roovers, J. *Macromolecules* 2001, 34, 244.

(16) Megan, N. E.; Barton, J. K. *Curr. Opin. Chem. Biol.* 2000, 4(2), 199. Szmacinski, H.; Terpetschnig, E.; Lakowicz, J. R. *Biophys. Chem.* 1996, 62(1-3), 109.

(17) Lakowicz, J. R. *Principles of Fluorescence Spectroscopy,* 2$^{nd}$ ed; Kluwer Academic and Plenum Publishers: New York, 1999. Joshi, H. S.; Tor, Y. *Chem. Commun.* 2001, 549.

(18) Staffilani, M.; Hoss, E.; Giesen, U.; Schneider E.; Hart, F.; Josel, H.-P.; Cola, L. D. *Inorg. Chem.* 2003, 42, 7789. Zhou, M.; Roovers, J.; Robertson, G. P.; Grover, C. P. *Anal. Chem.* 2003, 75, 6708.

(19) Chen, B. Z.; Sleiman, H. F. *Macromolecules* 2004, 37, 5866.

(20) Grubbs, R. H.; Tumas, W. *Science* 1989, 243, 907. Buchmeiser, M. R. *Chem. Rev.* 2000, 100, 1565.

(21) Bazan, G. C.; Khosravi, E.; Schrock, R. R.; Feast, W. J.; Gibson, V. C.; O'Regan, M. B.; Thomas, J. K.; Davis, W. M. *J. Am. Chem. Soc.* 1990, 112, 8378. Bazan, G. C.; Schrock, R. R.; Cho, H.; Gibson, V. C. *Macromolecules* 1991, 24, 4495. Nomura, K.; Takahashi, S.; Imanishi, Y. *Macromolecules* 2001, 34, 4712.

(22) Bielawski, C. W.; Scherman, O. A.; Grubbs, R. H. *Polymer* 2001, 42, 4939. Bielawski, C. W.; Benitez, D.; Morita, T.; Grubbs, R. H. *Macromolecules* 2001, 34, 8610. Maughon, B. R.; Morita, T.; Bielawski, C. W.; Grubbs, R. H. *Macromolecules* 2000, 33, 1929. Morita, T.; Maughon, B. R.; Bielawski, C. W.; Grubbs, R. H. *Macromolecules* 2000, 33, 6621. Bielawski, C. W.; Morita, T.; Grubbs, R. H. *Macromolecules* 2000, 33, 678. Katayama, H.; Fukuse, Y.; Nobuto, Y.; Akamatsu, K.; Ozawa, F. *Macromolecules* 2003, 36, 7020. Gibson, V. C.; Okada, T. *Macromolecules* 2000, 33, 655.

(23) Owen, R. M.; Gestwicki, J. E.; Young, T.; Kiessling, L. L. *Org. Lett.* 2002, 4, 2293.

What is claimed is:

1. A block copolymer of Formula:

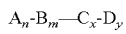

wherein:

"A" is a hydrophobic block comprising the structure:

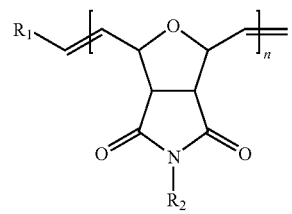

wherein:

$R_1$ is an aryl group;

$R_2$ is an alkyl group; and

"n" is an integer ranging from 1 to 75;

"B" is a luminescent block;

"C" is a hydrophilic block;

"D" is a molecular recognition unit;

"n" and "m" are integers ranging from 1 to 75;

"x" is either 0 or an integer ranging from 1 to 75; and

"Y" is either 0 or 1.

2. The block copolymer of claim 1, wherein:

"B" comprises the structure:

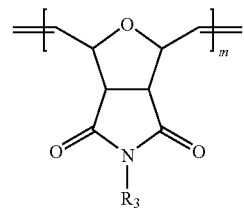

wherein "m" is an integer ranging from 1 to 75 and $R_3$ comprises the structure:

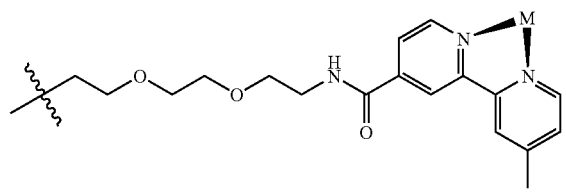

wherein "M" is selected from the group consisting of $Ru(bpy)_2^{2+}$; $Os(bpy)_2^{2+}$; $Ru(diphenylphosphinoethane)_2(CN)_2$; pyrene excimer; and $Pt(C\equiv C-Ph)_2$.

3. The block copolymer of claim 1, wherein:
"B" comprises the structure:

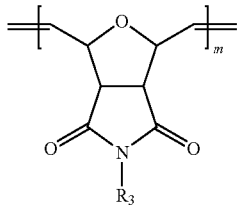

wherein "m" is an integer ranging from 1 to 75 and $R_3$ comprises the structure:

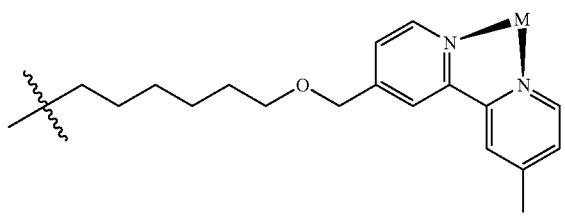

wherein "M" is selected from the group consisting of Ru(bpy)$_2^{2+}$; Os(bpy)$_2^{2+}$; Ru(diphenylphosphinoethane)$_2$(CN)$_2$; Pyrene excimer; and Pt(C≡C—Ph)$_2$.

4. The block copolymer of claim 1 wherein:
"C" comprises the structure:

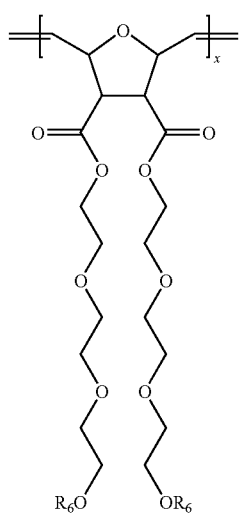

wherein "x" is either 0 or an integer ranging from 1 to 75 and $R_4$ comprises the structure:

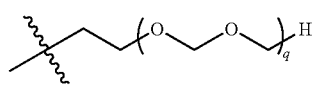

wherein q is an integer ranging from 1 to 100.

5. The block copolymer of claim 1 wherein:
"C" comprises the structure:

wherein "x" is either 0 or an integer ranging from 1 to 75 and $R_6$ is selected from the group consisting of H and Me.

6. The block copolymer of claim 1 wherein:
"C" comprises the structure:

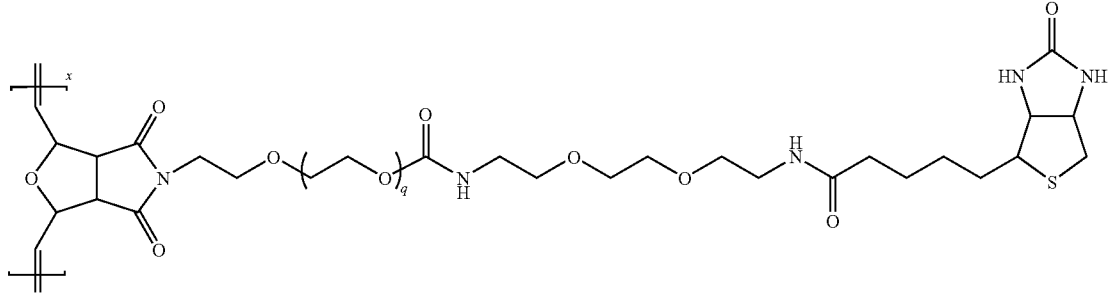

wherein "x" is either 0 or an integer ranging from 1 to 75 and wherein q is an integer ranging from 1 to 100.

7. The block copolymer of claim 1 wherein:
"D" comprises the structure:

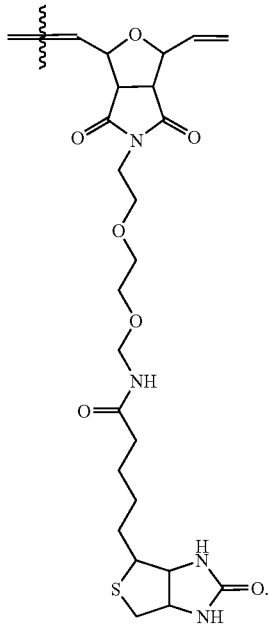

8. The block copolymer of claim 1 wherein:
"D" comprises the structure:

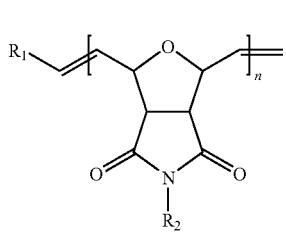

9. The block copolymer of claim 1 wherein:
"A" comprises the structure:

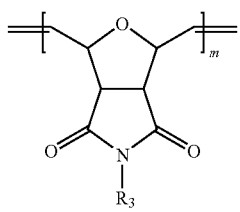

wherein:
$R_1$ is phenyl;
$R_2$ is butyl; and
"n" is 10;
"B" comprises the structure:

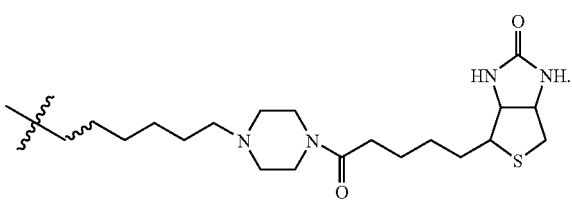

wherein "m" is 10 and $R_3$ comprises the structure:

wherein "M" is $Ru(bpy)_2^{2+}$;
"x" is 0;
"y" is 1; and
"D" comprises the structure:

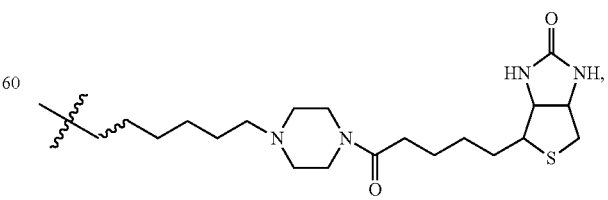

said block copolymer comprising the structure:
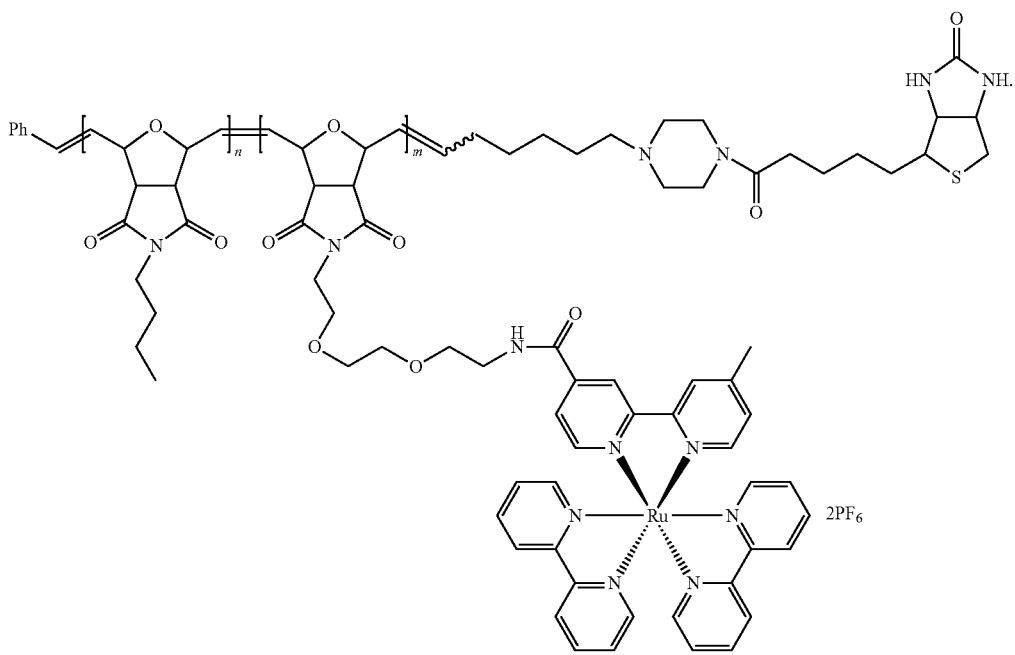
10. The block copolymer of claim 1 wherein:
"A" comprises the structure:
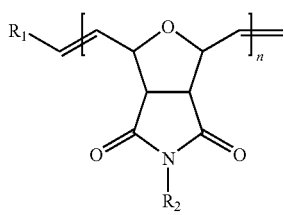
wherein:
$R_1$ is phenyl;
$R_2$ is butyl; and
"n" is 45;
"B" comprises the structure:
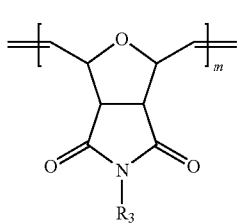
wherein "m" is 45 and $R_3$ comprises the structure:
wherein "M" is $Ru(bpy)_2^{2+}$;
"x" is 0;
"y" is 1; and
"D" comprises the structure:

said block copolymer comprising the structure:
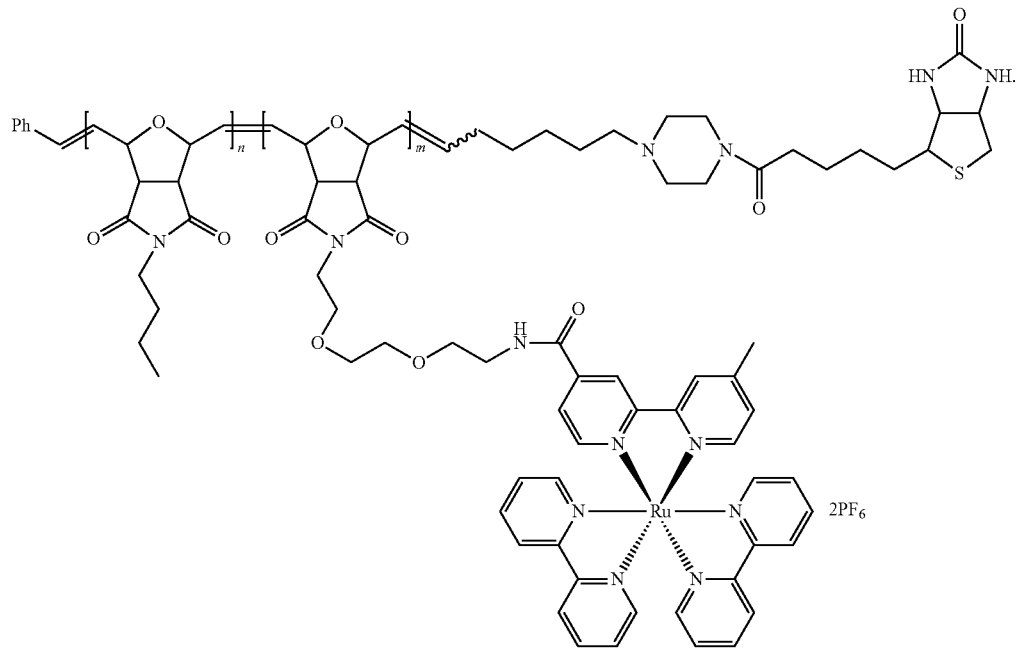
11. The block copolymer of claim 1 wherein:
"A" comprises the structure:
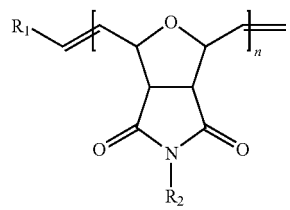
wherein:
R₁ is phenyl;
R₂ is butyl; and
"n" is 10;
"B" comprises the structure:
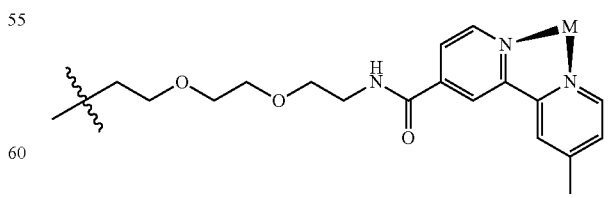
wherein "m" is 10 and R₃ comprises the structure:
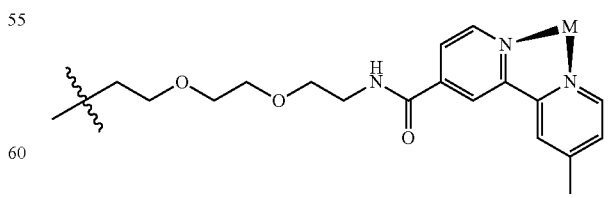
wherein "M" is $Ru(bpy)_2^{2+}$;
"x" and "y" are 0;

said block copolymer comprising the structure:
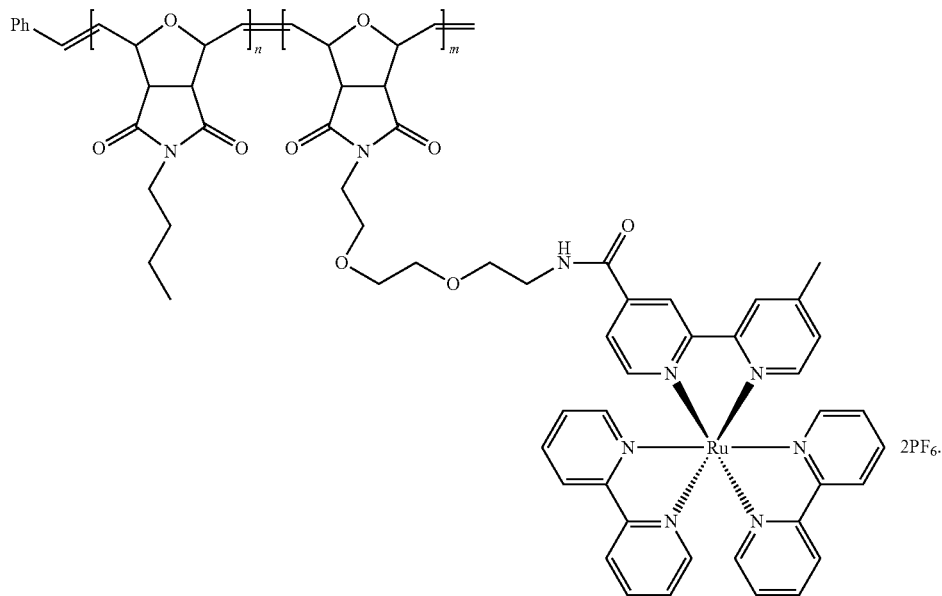
12. The block copolymer of claim 1 wherein:
"A" comprises the structure:
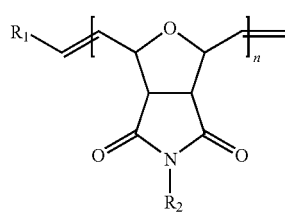
wherein:
$R_1$ is phenyl;
$R_2$ is butyl; and
"n" is 45;
"B" comprises the structure:
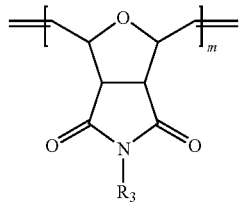
wherein "m" is 45 and $R_3$ comprises the structure:
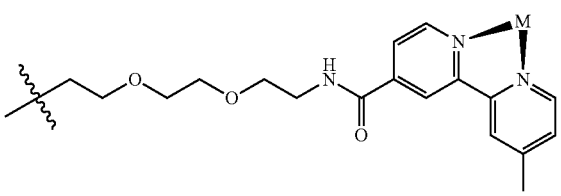
herein "M" is $Ru(bpy)_2^{2+}$;
"x" and "y" are 0;

said block copolymer comprising the structure:
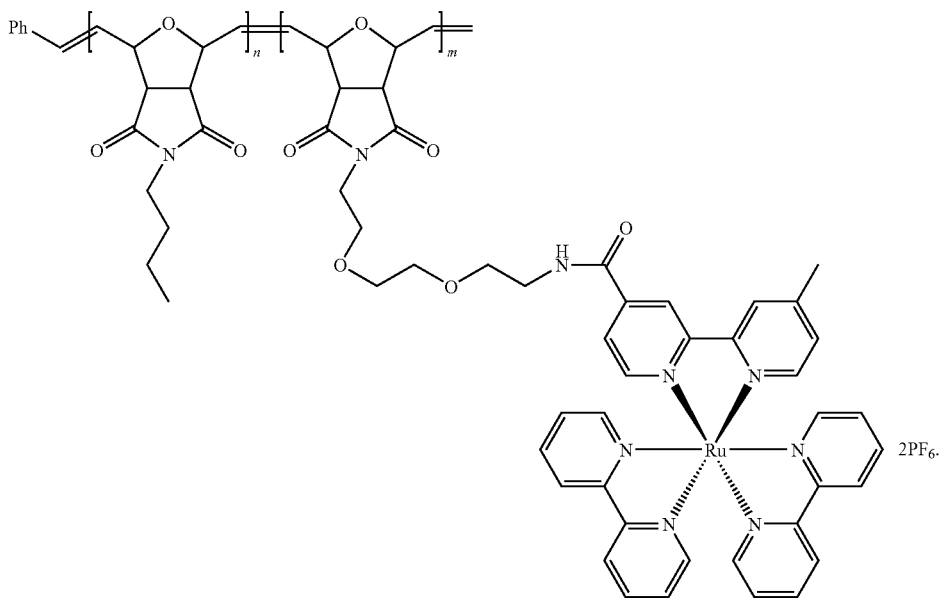
13. The block copolymer of claim 1 wherein:
"A" comprises the structure:
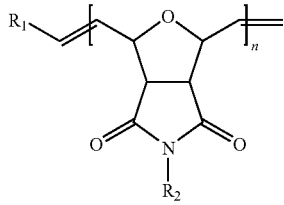
wherein:
R₁ is phenyl;
R₂ is butyl; and
"n" is 40;
"B" comprises the structure:
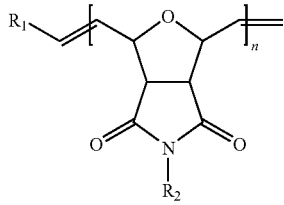
wherein "m" is 50 and R₃ comprises the structure:
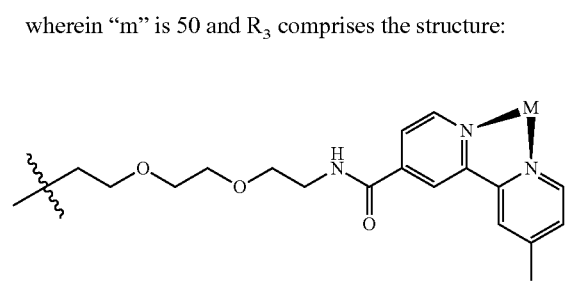
wherein "M" is Ru(bpy)$_2^{2+}$;
"C" comprises the structure:
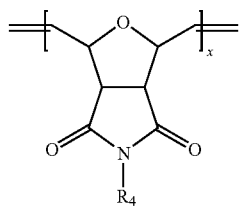
wherein "x" is 50 and R₄ comprises the structure:
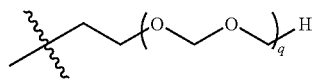
wherein q is 77;

"D" comprises the structure:
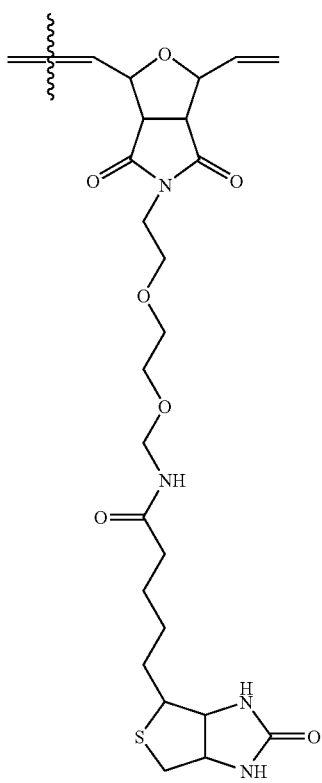
14. The block copolymer of claim 1 wherein:
"A" comprises the structure:
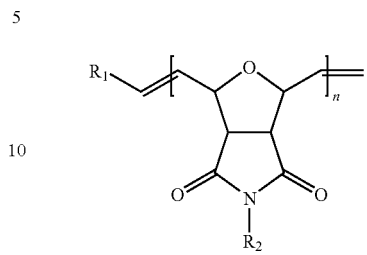
wherein:
R$_1$ is phenyl;
R$_2$ is butyl; and
"n" is selected from the group consisting of 10, 40, 45 and 50;
"B" comprises the structure:
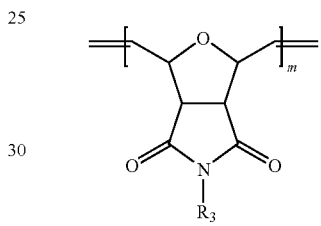
said block copolymer comprising the structure:
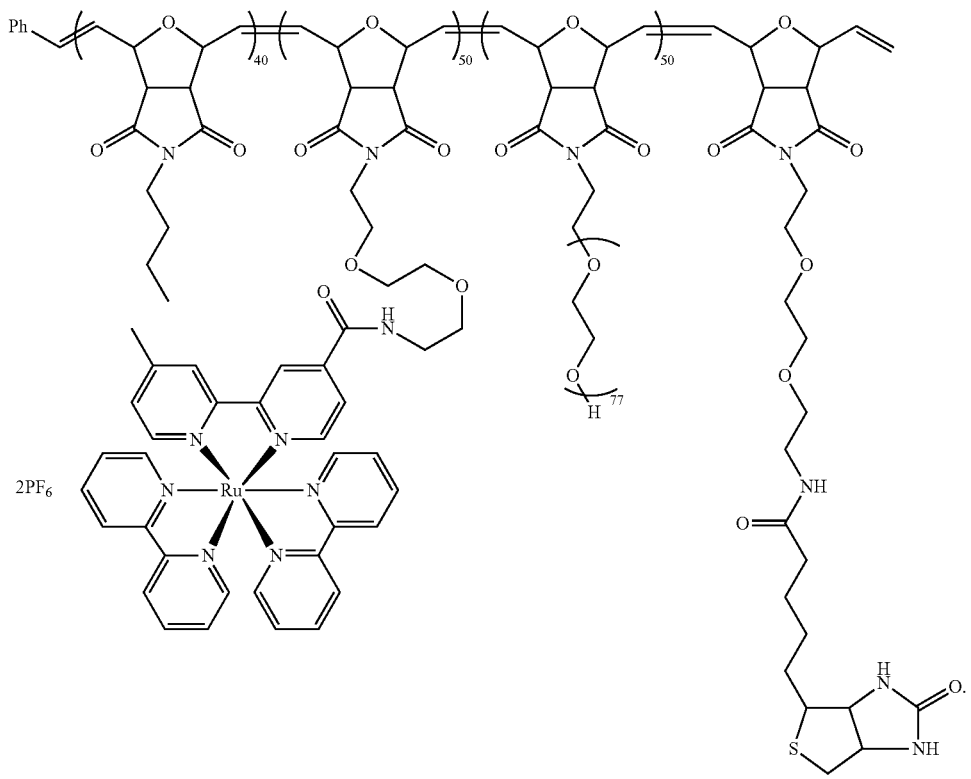

wherein "m" is selected from the group consisting of 10, 40, 45 and 50, and $R_3$ comprises the structure:

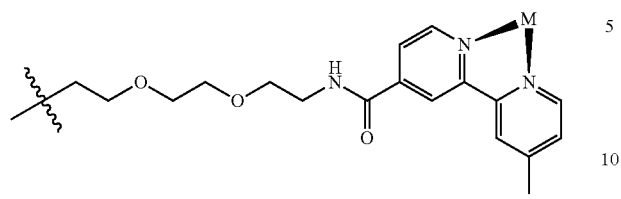

wherein "M" is Ru(bpy)$_2^{2+}$;
"C" comprises the structure:

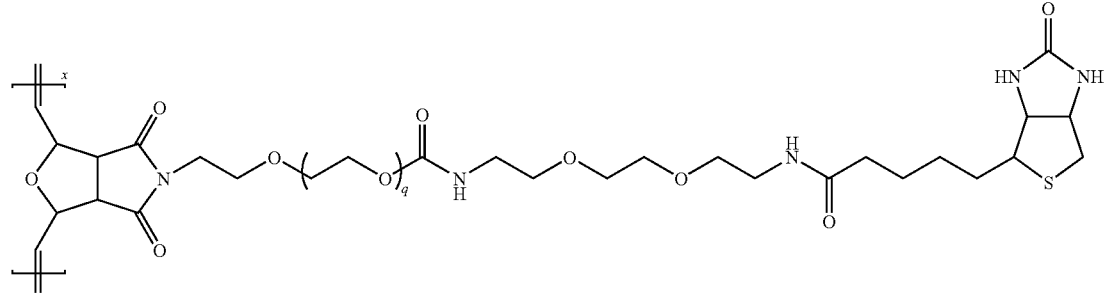

wherein "x" is 1 and wherein q is 77;
"y" is 0;
said block copolymer comprising the structure:

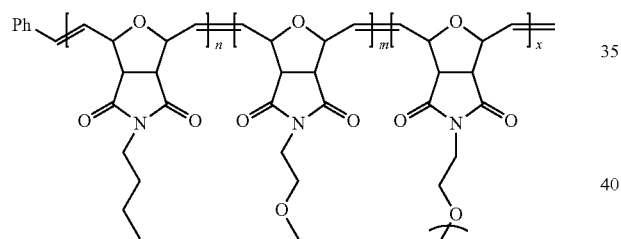
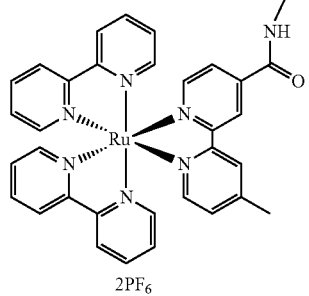
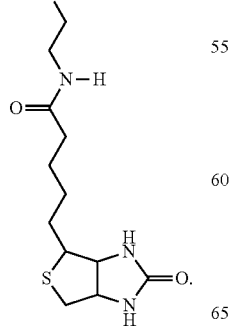

2PF$_6$

15. The block copolymer of claim 1 wherein:
"A" comprises the structure:

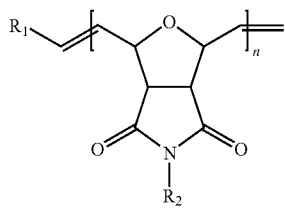

wherein:
R$_1$ is phenyl;
R$_2$ is butyl; and
"n" is selected from the group consisting of 10, 40, 45 and 50;
"B" comprises the structure:

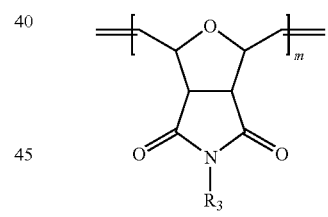

wherein "m" is selected from the group consisting of 10, 40, 45 and 50, and R$_3$ comprises the structure:

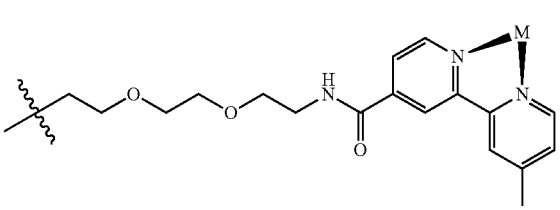

wherein "M" is Ru(bpy)$_2^{2+}$;

"C" comprises the structure:
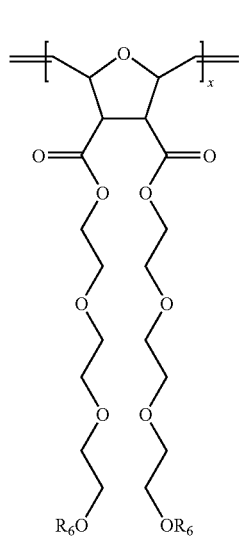
wherein "x" is selected from the group consisting of 10, 40, 45 and 50, and $R_6$ is selected from the group consisting of H and Me;
"D" comprises the structure:
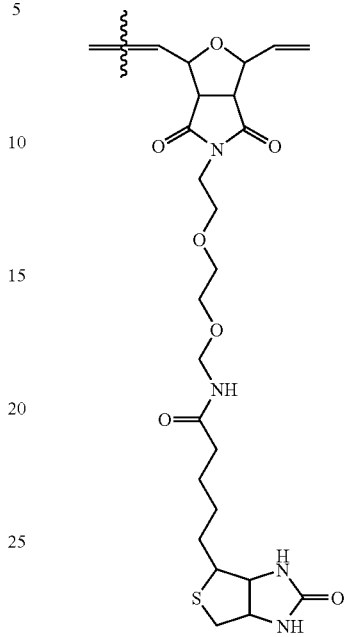
said block copolymer comprising the structure:
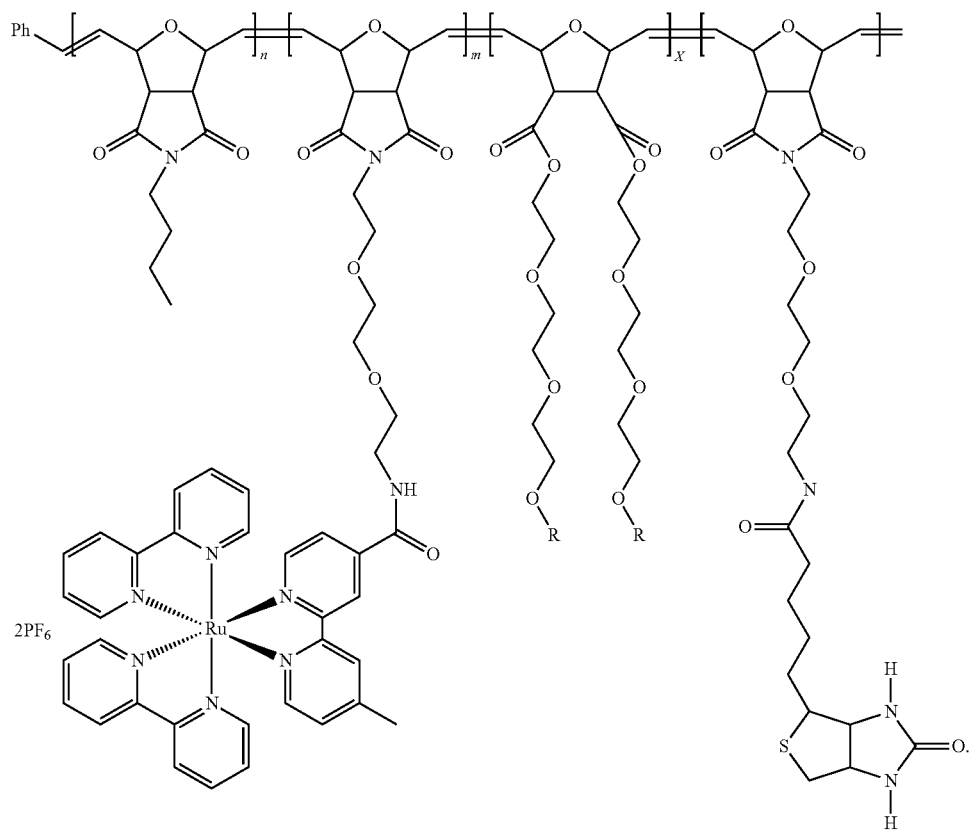

16. The block copolymer of claim 1 wherein:

"A" comprises the structure:

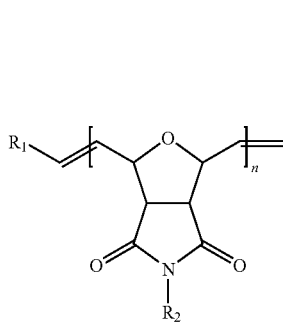

wherein:

R₁ is phenyl;

R₂ is butyl; and

"n" is selected from the group consisting of 10, 40, 45 and 50;

"B" comprises the structure:

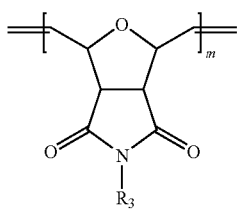

wherein "m" is selected from the group consisting of 10, 40, 45 and 50, and R₃ comprises the structure:

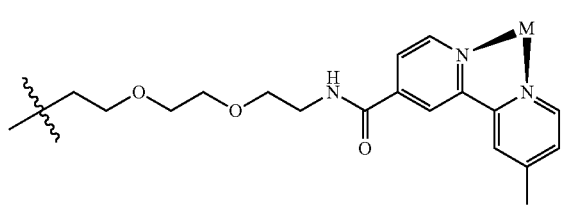

wherein "M" is $Ru(bpy)_2^{2+}$;

"C" comprises the structure:

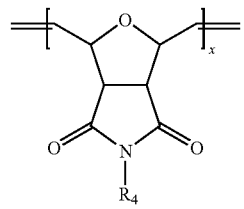

wherein "x" is selected from the group consisting of 10, 40, 45 and 50 and R₄ comprises the structure:

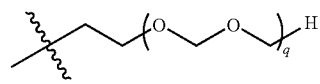

wherein q is 77;

"D" comprises the structure:

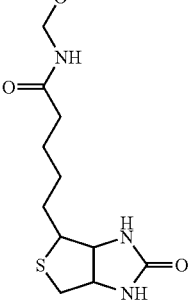

said block copolymer comprising the structure:
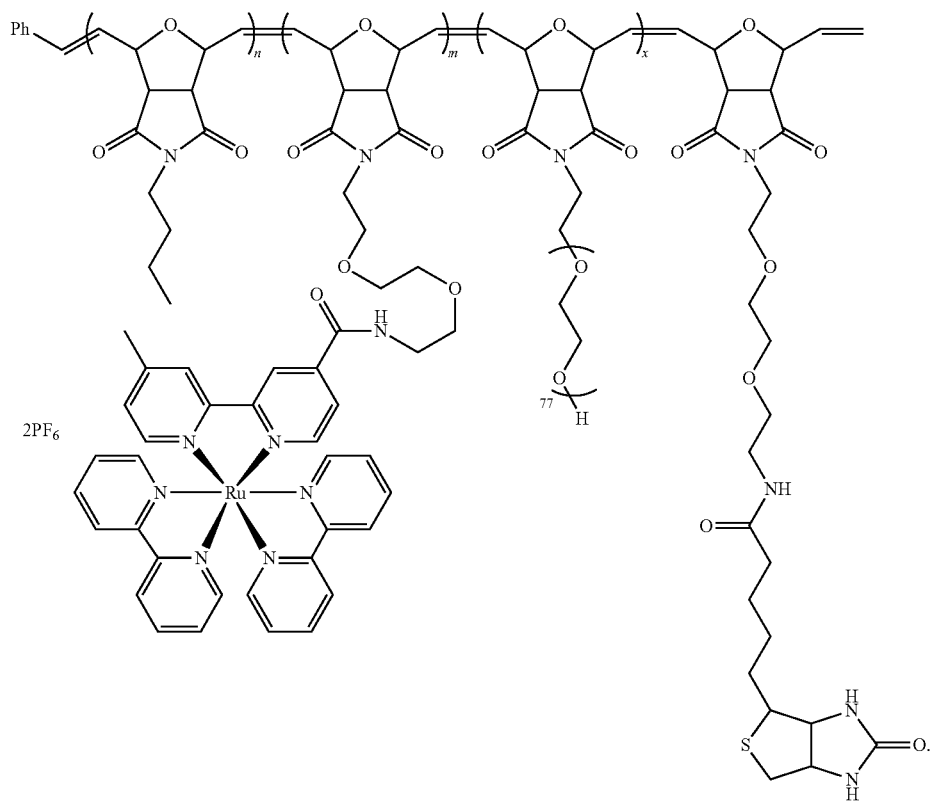
17. A nanoparticle comprising at least one block copolymer as defined in claim 1.
18. The nanoparticle of claim 17, having a size ranging from about 1 nm to about 1000 nm, preferably from about 2 nm to about 100 nm and more preferably ranging from about 20 nm to about 60 nm.
* * * * *

UNITED STATES PATENT AND TRADEMARK OFFICE
CERTIFICATE OF CORRECTION

PATENT NO. : 8,324,358 B2  
APPLICATION NO. : 11/914721  
DATED : December 4, 2012  
INVENTOR(S) : Hanadi Sleiman et al.

Page 1 of 1

It is certified that error appears in the above-identified patent and that said Letters Patent is hereby corrected as shown below:

In claim 1, column 40, line 10, delete "$A_n$-$B_m$—$C_x$-$D_y$" and insert --$A_n$—$B_m$—$C_x$—$D_y$-- therefor.

In claim 12, column 50, line 65, delete "herein" and insert --wherein-- therefor.

In claim 15, column 58, line 33, delete " 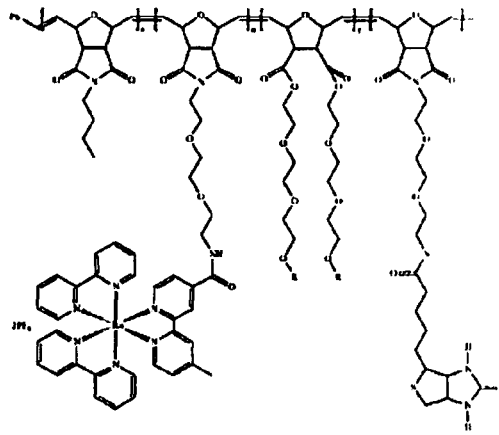 " and insert

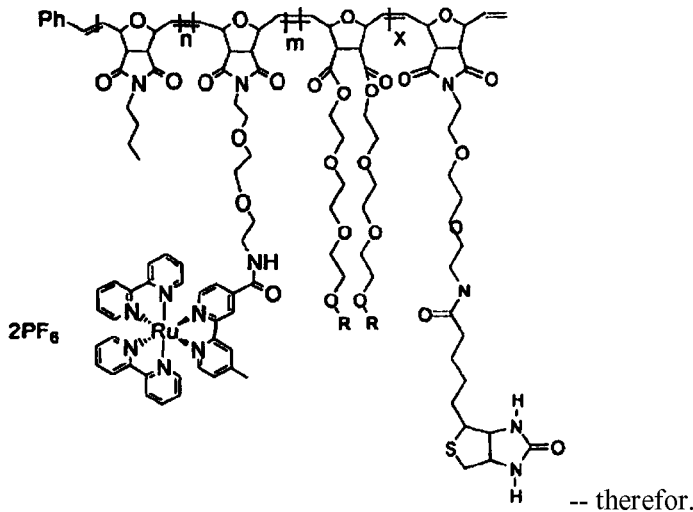

-- therefor.

Signed and Sealed this  
Fifteenth Day of January, 2013

David J. Kappos  
*Director of the United States Patent and Trademark Office*